US012558495B2

(12) United States Patent
Besson et al.

(10) Patent No.: US 12,558,495 B2
(45) Date of Patent: Feb. 24, 2026

(54) AUTO-INJECTOR WITH CAP

(71) Applicant: Becton Dickinson France, Le Pont-de-Claix (FR)

(72) Inventors: Nicolas Besson, Treffort (FR); Adrien Plouvier, Saint Martin d'Heres (FR)

(73) Assignee: Becton Dickinson France, Le Pont de Claix (FR)

( * ) Notice: Subject to any disclaimer, the term of this patent is extended or adjusted under 35 U.S.C. 154(b) by 1043 days.

(21) Appl. No.: 17/426,035

(22) PCT Filed: Feb. 26, 2020

(86) PCT No.: PCT/EP2020/055008
§ 371 (c)(1),
(2) Date: Aug. 25, 2021

(87) PCT Pub. No.: WO2020/173995
PCT Pub. Date: Sep. 3, 2020

(65) Prior Publication Data
US 2022/0134019 A1 May 5, 2022

(30) Foreign Application Priority Data

Feb. 26, 2019 (EP) ..................................... 19305227

(51) Int. Cl.
*A61M 5/32* (2006.01)
*A61M 5/31* (2006.01)

(52) U.S. Cl.
CPC ........ *A61M 5/3204* (2013.01); *A61M 5/3129* (2013.01); *A61M 5/3245* (2013.01);
(Continued)

(58) Field of Classification Search
CPC .............. A61M 5/3245; A61M 5/3219; A61M 5/3202; A61M 5/3204; A61M 5/326;
(Continued)

(56) References Cited

U.S. PATENT DOCUMENTS

| | | | |
|---|---|---|---|
| 3,562,564 | A | 2/1971 | Potter |
| 6,056,728 | A | 5/2000 | Von Schuckmann |

(Continued)

FOREIGN PATENT DOCUMENTS

| | | |
|---|---|---|
| CH | 712891 A2 | 3/2018 |
| CN | 103249617 A | 8/2013 |

(Continued)

*Primary Examiner* — Kevin C Sirmons
*Assistant Examiner* — Alexandra Lalonde
(74) *Attorney, Agent, or Firm* — The Webb Law Firm

(57) ABSTRACT

A drug delivery device (10) includes a housing (26), a syringe assembly (16) including a barrel (52), a stopper (54), a cannula (56), and a rigid needle shield (58) receiving at least a portion of the cannula, with at least a portion of the syringe assembly positioned within the housing, a drive assembly (40), with at least a portion of the drive assembly positioned within the housing, a cap (18) secured to the housing, with the cap including an outer portion (20) defining an interior space and a retainer (160) comprising a body with a removal projection (164) configured to remove the rigid needle shield upon axial movement of the outer portion of the cap away from the housing, and a needle cover (22) having a pre-use position, an actuation position, and a post-use position. The outer portion receives a portion of the needle cover, with the outer portion configured to prevent movement of the needle cover from the pre-use position to the actuation position.

14 Claims, 34 Drawing Sheets

(52) U.S. Cl.
CPC ..... *A61M 5/326* (2013.01); *A61M 2005/3131* (2013.01); *A61M 2005/3247* (2013.01); *A61M 2005/3264* (2013.01)

(58) Field of Classification Search
CPC .. A61M 2005/3131; A61M 2005/3247; A61M 2005/3264; A61M 2005/2013; A61M 5/3216; A61M 5/20; A61M 5/24; A61M 2005/2073; A61M 2005/312; A61M 2005/2026
See application file for complete search history.

(56) References Cited

U.S. PATENT DOCUMENTS

| | | | |
|---|---|---|---|
| 6,090,070 A | 7/2000 | Hager et al. |
| 6,183,446 B1 | 2/2001 | Jeanbourquin |
| 6,746,429 B2 | 6/2004 | Sadowski et al. |
| 7,112,187 B2 | 9/2006 | Karlsson |
| 7,357,790 B2 | 4/2008 | Hommann et al. |
| 7,442,185 B2 | 10/2008 | Amark et al. |
| 7,563,252 B2 | 7/2009 | Marshall et al. |
| 7,717,877 B2 | 5/2010 | Lavi et al. |
| 7,879,007 B2 | 2/2011 | Hommann |
| 7,988,675 B2 | 8/2011 | Gillespie, III et al. |
| 8,021,335 B2 | 9/2011 | Lesch, Jr. |
| 8,038,649 B2 | 10/2011 | Kronestedt |
| 8,062,255 B2 | 11/2011 | Brunnberg et al. |
| 8,172,797 B2 | 5/2012 | Hogdahl |
| 8,177,745 B2 | 5/2012 | Brechbuehler et al. |
| 8,317,751 B2 | 11/2012 | Habeshaw et al. |
| 8,337,472 B2 | 12/2012 | Edginton et al. |
| 8,376,998 B2 | 2/2013 | Daily et al. |
| 8,409,149 B2 | 4/2013 | Hommann et al. |
| 8,496,619 B2 | 7/2013 | Kramer et al. |
| 8,579,866 B2 | 11/2013 | Morgan et al. |
| 8,679,061 B2 | 3/2014 | Julian et al. |
| 8,715,246 B2 | 5/2014 | Giambattista et al. |
| 8,747,357 B2 | 6/2014 | Stamp et al. |
| 8,758,301 B2 | 6/2014 | Shang et al. |
| 8,915,882 B2 | 12/2014 | Cabiri |
| 8,932,254 B2 | 1/2015 | Eaton |
| 8,945,049 B2 | 2/2015 | Hommann et al. |
| 8,956,331 B2 | 2/2015 | Johansen et al. |
| 8,968,236 B2 | 3/2015 | Jennings et al. |
| 8,992,477 B2 | 3/2015 | Raday et al. |
| 8,998,855 B2 | 4/2015 | Hudson et al. |
| 9,011,375 B2 | 4/2015 | Holmqvist et al. |
| 9,033,932 B2 | 5/2015 | Holmqvist |
| 9,072,833 B2 | 7/2015 | Jennings et al. |
| 9,078,978 B2 | 7/2015 | Schraga |
| 9,084,849 B2 | 7/2015 | Edwards et al. |
| 9,125,988 B2 | 9/2015 | Karlsson |
| 9,180,256 B2 | 11/2015 | Eaton |
| 9,180,259 B2 | 11/2015 | Lesch, Jr. |
| 9,186,462 B2 | 11/2015 | Lanzi et al. |
| 9,199,038 B2 | 12/2015 | Daniel |
| 9,199,041 B2 | 12/2015 | Edginton |
| 9,205,199 B2 | 12/2015 | Kemp et al. |
| 9,216,251 B2 | 12/2015 | Daniel |
| 9,233,213 B2 | 1/2016 | Olson et al. |
| 9,259,536 B2 | 2/2016 | Gillespie, III et al. |
| 9,302,047 B2 | 4/2016 | Alexandersson |
| 9,327,084 B2 | 5/2016 | Evans |
| 9,352,099 B2 | 5/2016 | Roberts et al. |
| 9,358,345 B2 | 6/2016 | Brereton et al. |
| 9,364,610 B2 | 6/2016 | KraMer et al. |
| 9,364,611 B2 | 6/2016 | KraMer et al. |
| 9,427,528 B2 | 8/2016 | Hommann et al. |
| 9,427,531 B2 | 8/2016 | Hourmand et al. |
| 9,446,195 B2 | 9/2016 | Kramer et al. |
| 9,486,583 B2 | 11/2016 | Lannan et al. |
| 9,522,233 B2 | 12/2016 | Bicknell et al. |
| 9,526,837 B2 | 12/2016 | Carrel et al. |
| 9,533,099 B2 | 1/2017 | Maritan |
| 9,533,102 B2 | 1/2017 | Lesch, Jr. |
| 9,586,011 B2 | 3/2017 | Roberts et al. |
| 9,604,011 B2 | 3/2017 | Roberts et al. |
| 9,616,181 B2 | 4/2017 | Kemp et al. |
| 9,616,183 B2 | 4/2017 | Wozencroft |
| 9,629,959 B2 | 4/2017 | Lesch |
| 9,724,480 B2 | 8/2017 | Harms et al. |
| 9,744,306 B2 | 8/2017 | Cowe |
| 9,764,092 B2 | 9/2017 | Cabiri |
| 9,764,101 B2 | 9/2017 | McLoughlin et al. |
| 9,775,948 B2 | 10/2017 | Bechmann et al. |
| 9,789,257 B2 | 10/2017 | Travanty |
| 9,833,579 B2 | 12/2017 | Pedersen et al. |
| 9,855,392 B2 | 1/2018 | Hommann et al. |
| 9,867,942 B2 | 1/2018 | Alexandersson |
| 9,867,949 B2 | 1/2018 | Sund et al. |
| 9,872,961 B2 | 1/2018 | Fourt et al. |
| 9,901,674 B2 | 2/2018 | McLoughlin et al. |
| 9,913,943 B2 | 3/2018 | Fourt et al. |
| 9,925,342 B2 | 3/2018 | Carrel et al. |
| RE46,789 E | 4/2018 | Olson |
| 9,950,125 B2 | 4/2018 | Wotton et al. |
| 9,956,353 B2 | 5/2018 | Rao et al. |
| 9,974,904 B2 | 5/2018 | Burk et al. |
| 9,981,084 B2 | 5/2018 | Kadamus et al. |
| 9,987,436 B2 | 6/2018 | Giambattista et al. |
| 9,999,734 B2 | 6/2018 | Cowe |
| 10,004,852 B2 | 6/2018 | Marsh et al. |
| 10,046,115 B2 | 8/2018 | Bokelman et al. |
| 10,080,847 B2 | 9/2018 | Roberts et al. |
| 10,086,145 B2 | 10/2018 | Cabiri et al. |
| 10,086,152 B2 | 10/2018 | Imai et al. |
| 10,092,073 B2 | 10/2018 | Wagoner |
| 10,092,698 B2 | 10/2018 | Park et al. |
| 10,092,703 B2 | 10/2018 | Mounce et al. |
| 10,105,496 B2 | 10/2018 | Aneas |
| 10,118,001 B2 | 11/2018 | Fourt et al. |
| 10,130,774 B2 | 11/2018 | Daniel |
| 10,137,255 B2 | 11/2018 | Kemp |
| 10,137,256 B2 | 11/2018 | Taal et al. |
| 10,149,939 B2 | 12/2018 | Giambattista et al. |
| 10,159,791 B2 | 12/2018 | Guillermo |
| 10,159,800 B2 | 12/2018 | Säll |
| 10,183,121 B2 | 1/2019 | Cowe |
| 10,188,802 B2 | 1/2019 | Hodgson |
| 10,252,005 B2 | 4/2019 | Row et al. |
| 10,272,210 B2 | 4/2019 | Keitel |
| 10,300,218 B2 | 5/2019 | Stefanov |
| 10,307,545 B2 | 6/2019 | Maxfield |
| 10,322,237 B2 | 6/2019 | Fabien |
| 10,335,553 B2 | 7/2019 | Bendek |
| 10,350,356 B2 | 7/2019 | Hirschel et al. |
| 10,363,377 B2 | 7/2019 | Atterbury et al. |
| 10,363,378 B2 | 7/2019 | Moore |
| 10,376,641 B2 | 8/2019 | Hirschel et al. |
| 10,384,009 B2 | 8/2019 | Olson et al. |
| 10,398,848 B2 | 9/2019 | Mosebach et al. |
| 10,406,294 B2 | 9/2019 | Ward et al. |
| 10,417,937 B2 | 9/2019 | Gaillot et al. |
| 10,441,728 B2 | 10/2019 | Schader et al. |
| 10,485,934 B2 | 11/2019 | Bostrom |
| 10,493,212 B2 | 12/2019 | Tschirren et al. |
| 10,493,213 B2 | 12/2019 | Hommann et al. |
| 10,500,337 B2 | 12/2019 | Fabien et al. |
| 10,525,201 B2 | 1/2020 | Brunnberg et al. |
| 10,561,798 B2 | 2/2020 | Holland et al. |
| 10,643,744 B2 | 5/2020 | Hopper et al. |
| 10,646,643 B2 | 5/2020 | Cabiri et al. |
| 10,758,683 B2 | 9/2020 | Gibson et al. |
| 10,799,647 B2 | 10/2020 | Hostettler et al. |
| 10,821,072 B2 | 11/2020 | Wotton et al. |
| 10,842,937 B2 | 11/2020 | Schader et al. |
| 10,881,799 B2 | 1/2021 | Hirschel et al. |
| 10,888,668 B2 | 1/2021 | Mosebach et al. |
| 10,894,127 B2 | 1/2021 | Tschirren et al. |
| 10,912,890 B2 | 2/2021 | Gaillot et al. |
| 10,918,798 B2 | 2/2021 | Helmer |
| 10,967,128 B2 | 4/2021 | Holmqvist |
| 10,973,984 B2 | 4/2021 | Fournier et al. |

(56)　　　　　References Cited

U.S. PATENT DOCUMENTS

| | | | |
|---|---|---|---|
| 11,040,142 B2 | 6/2021 | Sarkorov et al. | |
| 11,040,145 B1 | 6/2021 | Chu | |
| 11,097,065 B2 | 8/2021 | Newton et al. | |
| 11,103,647 B2 | 8/2021 | Bernhard et al. | |
| 11,141,542 B2 | 10/2021 | Chu et al. | |
| 11,147,932 B2 | 10/2021 | Alexandersson | |
| 11,246,987 B2 | 2/2022 | Cowe et al. | |
| 2003/0105430 A1 | 6/2003 | Lavi et al. | |
| 2005/0222539 A1 | 10/2005 | Gonzales et al. | |
| 2011/0144594 A1 | 6/2011 | Sund et al. | |
| 2011/0196339 A1 | 8/2011 | Hirschel et al. | |
| 2012/0191047 A1 | 7/2012 | Raday et al. | |
| 2013/0331796 A1 | 12/2013 | Wozencroft | |
| 2014/0128808 A1 | 5/2014 | Keitel | |
| 2014/0243753 A1* | 8/2014 | Bostrom | A61M 5/3202 |
| | | | 604/198 |
| 2014/0257193 A1* | 9/2014 | Bostrom | A61M 5/2033 |
| | | | 604/197 |
| 2014/0288503 A1 | 9/2014 | Julian et al. | |
| 2015/0088077 A1 | 3/2015 | Kemp et al. | |
| 2015/0174325 A1 | 6/2015 | Young et al. | |
| 2015/0202379 A1 | 7/2015 | Raday et al. | |
| 2015/0273162 A1 | 10/2015 | Holmqvist | |
| 2016/0030675 A1 | 2/2016 | Draper et al. | |
| 2016/0074584 A1 | 3/2016 | Carmel et al. | |
| 2016/0074585 A1 | 3/2016 | Hommann et al. | |
| 2016/0106929 A1 | 4/2016 | Fournier et al. | |
| 2016/0129195 A1 | 5/2016 | Jennings et al. | |
| 2016/0129200 A1 | 5/2016 | Jennings et al. | |
| 2016/0144132 A1 | 5/2016 | Scanlon | |
| 2016/0151586 A1 | 6/2016 | Kemp | |
| 2016/0175523 A1 | 6/2016 | Blomberg | |
| 2016/0199588 A1* | 7/2016 | Kemp | A61M 5/2033 |
| | | | 604/193 |
| 2016/0199589 A1 | 7/2016 | Plumptre | |
| 2016/0220761 A1 | 8/2016 | Shetty et al. | |
| 2016/0303323 A1 | 10/2016 | Saussaye et al. | |
| 2016/0303327 A1 | 10/2016 | Moren | |
| 2016/0317750 A1 | 11/2016 | Jugl et al. | |
| 2016/0317753 A1 | 11/2016 | Jugl et al. | |
| 2016/0325044 A1 | 11/2016 | Tschirren et al. | |
| 2017/0007764 A1 | 1/2017 | Saussaye | |
| 2017/0007765 A1 | 1/2017 | Cowe et al. | |
| 2017/0021103 A1 | 1/2017 | Mosebach et al. | |
| 2017/0043103 A1 | 2/2017 | Wotton et al. | |
| 2017/0072142 A1 | 3/2017 | Perthu | |
| 2017/0080163 A1 | 3/2017 | Bendek et al. | |
| 2017/0106146 A1* | 4/2017 | Folk | A61M 5/20 |
| 2017/0136192 A1 | 5/2017 | Stefansen et al. | |
| 2017/0173270 A1 | 6/2017 | Nakamura et al. | |
| 2017/0182242 A1 | 6/2017 | Galitz et al. | |
| 2017/0203041 A1 | 7/2017 | Julian et al. | |
| 2017/0224921 A1 | 8/2017 | Takabatake et al. | |
| 2017/0252518 A1 | 9/2017 | Holmqvist | |
| 2017/0258998 A1 | 9/2017 | Stamp | |
| 2017/0290990 A1 | 10/2017 | Wu | |
| 2017/0340824 A1 | 11/2017 | Maritan | |
| 2017/0361015 A1 | 12/2017 | McCullough | |
| 2017/0361021 A1 | 12/2017 | Wotton et al. | |
| 2018/0015223 A1 | 1/2018 | Aeschlimann | |
| 2018/0028753 A1 | 2/2018 | Wilmot et al. | |
| 2018/0036491 A1 | 2/2018 | Maxfield | |
| 2018/0036492 A1 | 2/2018 | Schader et al. | |
| 2018/0043108 A1 | 2/2018 | Mesa et al. | |
| 2018/0078713 A1 | 3/2018 | Hommann et al. | |
| 2018/0079119 A1 | 3/2018 | Morris et al. | |
| 2018/0093046 A1 | 4/2018 | Hourmand et al. | |
| 2018/0099099 A1 | 4/2018 | Sund et al. | |
| 2018/0110926 A1 | 4/2018 | Schrul et al. | |
| 2018/0110936 A1 | 4/2018 | Hatch et al. | |
| 2018/0126083 A1 | 5/2018 | Schmid et al. | |
| 2018/0133407 A1 | 5/2018 | Kemp et al. | |
| 2018/0140781 A1 | 5/2018 | Kemp et al. | |
| 2018/0140782 A1 | 5/2018 | Kemp et al. | |
| 2018/0147358 A1 | 5/2018 | Julian et al. | |
| 2018/0154078 A1 | 6/2018 | Mosebach et al. | |
| 2018/0154085 A1 | 6/2018 | Mosebach et al. | |
| 2018/0154089 A1 | 6/2018 | Mosebach et al. | |
| 2018/0161504 A1 | 6/2018 | Kemp et al. | |
| 2018/0169342 A1 | 6/2018 | Mosebach et al. | |
| 2018/0169349 A1 | 6/2018 | Mosebach et al. | |
| 2018/0177952 A1 | 6/2018 | Bengtsson et al. | |
| 2018/0200445 A1 | 7/2018 | Brereton et al. | |
| 2018/0207363 A1 | 7/2018 | Fabien et al. | |
| 2018/0221589 A1 | 8/2018 | Vogt et al. | |
| 2018/0228984 A1 | 8/2018 | Sall | |
| 2018/0243506 A1 | 8/2018 | Niven et al. | |
| 2018/0256826 A1 | 9/2018 | Roberts et al. | |
| 2018/0264196 A1 | 9/2018 | Fabien et al. | |
| 2018/0289899 A1 | 10/2018 | Gould | |
| 2018/0296768 A1 | 10/2018 | Gould et al. | |
| 2018/0304014 A1 | 10/2018 | Knudsen et al. | |
| 2018/0311438 A1 | 11/2018 | Stamp et al. | |
| 2018/0326152 A1 | 11/2018 | Laiosa | |
| 2018/0344946 A1 | 12/2018 | Scharf | |
| 2018/0353695 A1 | 12/2018 | Helmer | |
| 2018/0353705 A1 | 12/2018 | Andre et al. | |
| 2018/0369497 A1 | 12/2018 | Schader et al. | |
| 2019/0046735 A1 | 2/2019 | Ingerslev et al. | |
| 2019/0151547 A1 | 5/2019 | Cowe et al. | |
| 2019/0151564 A1 | 5/2019 | Schrul et al. | |
| 2019/0151565 A1 | 5/2019 | Groetzbach et al. | |
| 2019/0167908 A1 | 6/2019 | Fitzgibbon et al. | |
| 2019/0201634 A1 | 7/2019 | Newton et al. | |
| 2019/0209786 A1 | 7/2019 | Tschirren et al. | |
| 2019/0240394 A1 | 8/2019 | Horvath et al. | |
| 2019/0269856 A1 | 9/2019 | Baumeyer et al. | |
| 2019/0328968 A1 | 10/2019 | Giambattista | |
| 2020/0009323 A1 | 1/2020 | Nair et al. | |
| 2020/0030539 A1 | 1/2020 | Shabudin, Jr. | |
| 2020/0030547 A1 | 1/2020 | Wang et al. | |
| 2020/0033069 A1 | 1/2020 | Nakamura et al. | |
| 2020/0035047 A1 | 1/2020 | Arnold | |
| 2020/0046910 A1 | 2/2020 | Maxfield et al. | |
| 2020/0061309 A1 | 2/2020 | Alexandersson | |
| 2020/0139046 A1 | 5/2020 | Jacobsen | |
| 2020/0147311 A1 | 5/2020 | Dugand et al. | |
| 2020/0164138 A1 | 5/2020 | Holmqvist | |
| 2020/0254181 A1 | 8/2020 | Mosebach et al. | |
| 2020/0289740 A1 | 9/2020 | Tamtoro et al. | |
| 2020/0330699 A1 | 10/2020 | Burren et al. | |
| 2021/0015741 A1 | 1/2021 | Wotton et al. | |
| 2021/0085884 A1 | 3/2021 | Liniger et al. | |
| 2021/0093790 A1 | 4/2021 | Mosebach et al. | |
| 2021/0106756 A1 | 4/2021 | Alexandersson | |
| 2021/0268201 A1 | 9/2021 | Boström | |
| 2021/0275750 A1 | 9/2021 | Helmer et al. | |
| 2022/0016359 A1 | 1/2022 | Alexandersson | |

FOREIGN PATENT DOCUMENTS

| | | |
|---|---|---|
| CN | 103920212 A | 7/2014 |
| CN | 109069749 A | 12/2018 |
| DE | 102004060146 C5 | 12/2015 |
| EP | 2083887 B1 | 2/2011 |
| EP | 2323717 B1 | 5/2013 |
| EP | 2525845 B1 | 8/2014 |
| EP | 2823841 A1 | 1/2015 |
| EP | 2588168 B1 | 3/2015 |
| EP | 2878321 A1 | 6/2015 |
| EP | 2886144 A1 | 6/2015 |
| EP | 2731653 B1 | 10/2015 |
| EP | 2931338 B1 | 11/2016 |
| EP | 3235530 A1 | 10/2017 |
| EP | 3320932 A1 | 5/2018 |
| EP | 3107605 B1 | 9/2018 |
| EP | 2654854 B1 | 10/2018 |
| EP | 1850892 B1 | 1/2019 |
| EP | 3539594 A1 | 9/2019 |
| EP | 3541453 A1 | 9/2019 |
| EP | 2953667 B1 | 10/2019 |
| EP | 3407939 B1 | 10/2019 |
| EP | 3490647 B1 | 10/2021 |
| JP | 2013534164 A | 9/2013 |

(56) References Cited

FOREIGN PATENT DOCUMENTS

| | | | |
|---|---|---|---|
| JP | 2014503282 | A | 2/2014 |
| JP | 2015516845 | A | 6/2015 |
| JP | 2016538058 | A | 12/2016 |
| JP | 2017508548 | A | 3/2017 |
| JP | 2017525420 | A | 9/2017 |
| JP | 2018535052 | A | 11/2018 |
| KR | 1020150097784 | A | 8/2015 |
| KR | 1020170048508 | A | 5/2017 |
| RU | 2671419 | C2 | 10/2018 |
| TW | 201729859 | A | 9/2017 |
| WO | 03041768 | A1 | 5/2003 |
| WO | 2003047663 | A3 | 6/2003 |
| WO | 2004098687 | A1 | 11/2004 |
| WO | 2005097238 | A3 | 10/2005 |
| WO | 2008059233 | A1 | 5/2008 |
| WO | 2009019436 | A1 | 2/2009 |
| WO | 2009019437 | A1 | 2/2009 |
| WO | 2009019438 | A1 | 2/2009 |
| WO | 2009019439 | A1 | 2/2009 |
| WO | 2009019440 | A1 | 2/2009 |
| WO | 2009081103 | A1 | 7/2009 |
| WO | 2009090499 | A2 | 7/2009 |
| WO | 2009143255 | A1 | 11/2009 |
| WO | 2012045350 | A1 | 4/2012 |
| WO | 2012164397 | A1 | 12/2012 |
| WO | 2013006119 | A1 | 1/2013 |
| WO | 2013152323 | A1 | 10/2013 |
| WO | 2015132234 | A1 | 9/2015 |
| WO | 2016193344 | A1 | 12/2016 |
| WO | 2016193346 | A1 | 12/2016 |
| WO | 2017089269 | A1 | 6/2017 |
| WO | 2017089281 | A1 | 6/2017 |
| WO | 2017187177 | | 11/2017 |
| WO | 2017223354 | A1 | 12/2017 |
| WO | 2018004842 | A1 | 1/2018 |
| WO | 2018010947 | A1 | 1/2018 |
| WO | 2018018164 | A1 | 2/2018 |
| WO | 2018018165 | A1 | 2/2018 |
| WO | 2018018167 | A1 | 2/2018 |
| WO | 2018037034 | A1 | 3/2018 |
| WO | 2018053657 | A1 | 3/2018 |
| WO | 2018060745 | A1 | 4/2018 |
| WO | 2018069031 | A1 | 4/2018 |
| WO | 2018082886 | A1 | 5/2018 |
| WO | 2018091262 | A1 | 5/2018 |
| WO | 2018167640 | A1 | 9/2018 |
| WO | 2018172223 | A1 | 9/2018 |
| WO | 2018178127 | A8 | 10/2018 |
| WO | 2018192750 | A1 | 10/2018 |
| WO | 2018197774 | | 11/2018 |
| WO | 2018206583 | A1 | 11/2018 |
| WO | 2018215271 | A1 | 11/2018 |
| WO | 2018226565 | A1 | 12/2018 |
| WO | 2020015986 | A1 | 1/2020 |

* cited by examiner

AUTO-INJECTOR WITH CAP

CROSS-REFERENCE TO RELATED APPLICATIONS

This application is the United States national phase of International Application No. PCT/EP2020/055008 filed Feb. 26, 2020, and claims priority to Europe patent Application No. 19305227.1 filed Feb. 26, 2019, the entire disclosures of which are hereby incorporated by reference in their entirety.

BACKGROUND OF THE INVENTION

Field of the Disclosure

The present disclosure relates generally to a drug delivery device and, more specifically, to an auto-injector.

Description of the Related Art

Various types of automatic injection devices have been developed to allow drug solutions and other liquid therapeutic preparations to be administered by untrained personnel or to be self-injected. Generally, these devices include a reservoir that is pre-filled with the liquid therapeutic preparation, and some type of automatic needle-injection mechanism that can be triggered by the user. Many of these devices, such as auto-injectors, are designed so that the reservoir, such as a pre-filled syringe, is assembled into the device during assembly of the device. In addition to automatically deploying the needle-injection mechanism, many drug delivery devices also automatically shield the needle after use of the device to prevent any unintended contact with the needle.

SUMMARY OF THE INVENTION

In one aspect, a drug delivery device includes a housing, a syringe assembly including a barrel, a stopper, a cannula, and a rigid needle shield receiving at least a portion of the cannula, with at least a portion of the syringe assembly positioned within the housing, a drive assembly configured to move the stopper within the barrel upon actuation of the drive assembly, with at least a portion of the drive assembly positioned within the housing, a cap secured to the housing, with the cap including an outer portion defining an interior space and a retainer comprising a body with a removal projection configured to remove the rigid needle shield upon axial movement of the outer portion of the cap away from the housing, and a needle cover having a pre-use position where the cannula is positioned within the needle cover, an actuation position where the drive assembly is actuated, and a post-use position where the cannula is positioned within the needle cover. The outer portion receives a portion of the needle cover, with the outer portion configured to prevent movement of the needle cover from the pre-use position to the actuation position.

The outer portion includes a protrusion received by a cap opening defined by the needle cover, with the protrusion of the outer portion configured to engage the needle cover upon movement of the needle cover from the pre-use position to the actuation position.

A portion of the retainer may be received within the interior space of the outer portion, with the retainer secured to and axially moveable relative to the outer portion. The outer portion may include a retaining tab received by a retainer opening defined by the body of the retainer, with the retaining tab disengaged from the body of the retainer when the outer portion is secured to the housing, and the retaining tab of the outer portion configured to engage the retainer upon axial movement of the outer portion away from the housing and upon axial movement of the outer portion relative to the retainer. The retainer may include a pair of wings extending radially outward from the body of the retainer, with each wing configured to engage a rib extending radially inward from a body of the outer portion.

The retaining tab may extend radially outward through the retainer opening of the retainer. The retaining tab of the outer portion may be secured to the body of the cap via an extension arm, with the retaining tab moveable radially inward via the extension arm. The retainer may include a flange engaged with the outer portion when the outer portion is secured to the housing. The flange of the retainer may be spaced from the outer portion upon axial movement of the outer portion away from the housing. The surface of the removal projection may be planar and the corresponding surface of the rigid needle shield may be planar.

The body of the retainer may include a first end and a second end positioned opposite the first end, with the removal projection extending radially inward from body of the retainer via a removal arm, and the removal arm extending radially inward and in a direction extending from the second end of the body to the first end of the body. The removal projection may be moveable relative to the body of the retainer via the removal arm.

The device may further include a syringe holder positioned within the housing, with the syringe holder receiving the syringe assembly, and the syringe holder moveable relative to the housing. The syringe holder may be disengaged with the drive assembly when the outer portion is secured to the housing, with the syringe holder engaged with the drive assembly upon axial movement of the outer portion away from the housing.

A surface of the removal projection may be configured to engage a corresponding surface of the rigid needle shield to remove the rigid needle shield upon axial movement of the outer portion of the cap away from the housing, with the surface of the removal projection is disengaged from the corresponding surface of the rigid needle shield when the outer portion is secured to the housing. The protrusion may be configured to be removed from the cap opening before the surface of the removal projection engages the corresponding surface of the rigid needle shield upon axial movement of the outer portion away from the housing.

The outer portion may include one of a lock protrusion and a lock recess and the housing may include the other of the lock protrusion and the lock recess, with the lock protrusion received by the lock recess to secure the outer portion to the housing, and where the lock protrusion is separated from the lock recess before the surface of the removal projection engages the corresponding surface of the rigid needle shield upon axial movement of the outer portion away from the housing.

The device may include one or several of the following features, taken individually or according to all technical possible combinations:

the drug delivery device may comprise: a housing; a syringe assembly comprising a barrel, a stopper, a cannula, and a rigid needle shield receiving at least a portion of the cannula, at least a portion of the syringe assembly positioned within the housing; a drive assembly configured to move the stopper within the barrel upon actuation of the drive assembly, at least a portion of the drive assembly positioned within the housing; a cap secured to the housing, the cap comprises an outer portion defining an interior space and a retainer comprising a body with a removal projection, the removal projection configured to remove the rigid needle shield upon axial movement of the outer portion of the cap away from the housing, and a needle cover having a pre-use position where the cannula is positioned within the needle cover, an actuation position where the drive assembly is actuated, and a post-use position where the cannula is positioned within the needle cover, wherein the outer portion receives a portion of the needle cover, the outer portion configured to prevent movement of the needle cover from the pre-use position to the actuation position;

the outer portion may include a protrusion received by a cap opening defined by the needle cover, the protrusion of the outer portion is configured to engage the needle cover upon movement of the needle cover from the pre-use position to the actuation position;

a portion of the retainer may be received within the interior space of the outer portion of the cap, and wherein the retainer is secured to and axially moveable relative to the outer portion.

the outer portion may comprise a retaining tab received by a retainer opening defined by the body of the retainer, the retaining tab is disengaged from the body of the retainer when the outer portion is secured to the housing, the retaining tab of the outer portion is configured to engage the retainer upon axial movement of the outer portion away from the housing and upon axial movement of the outer portion relative to the retainer;

the retainer may comprise a pair of wings extending radially outward from the body of the retainer, each wing configured to engage a rib extending radially inward from a body of the outer portion;

the retaining tab may extend radially outward through the retainer opening of the retainer;

the retaining tab of the outer portion may be secured to the body of the outer portion via an extension arm, the retaining tab moveable radially inward via the extension arm;

the retainer may comprise a flange engaged with the outer portion when the outer portion is secured to the housing.

the flange of the retainer may be spaced from the outer portion upon axial movement of the outer portion away from the housing;

the surface of the removal projection may be planar, and wherein the corresponding surface of the rigid needle shield is planar.

the body of the retainer may comprise a first end and a second end positioned opposite the first end, the removal projection extending radially inward from the body of the retainer via a removal arm, the removal arm extending radially inward and in a direction extending from the second end of the body to the first end of the body;

the removal projection is moveable relative to the body of the retainer via the removal arm;

a syringe holder may be positioned within the housing, the syringe holder receiving the syringe assembly, the syringe holder moveable relative to the housing, wherein the syringe holder is disengaged with the drive assembly when the outer portion is secured to the housing, and wherein the syringe holder is engaged with the drive assembly upon axial movement of the outer portion away from the housing;

a surface of the removal projection may be configured to engage a corresponding surface of the rigid needle shield to remove the rigid needle shield upon axial movement of the outer portion of the cap away from the housing, the surface of the removal projection is disengaged from the corresponding surface of the rigid needle shield when the outer portion is secured to the housing;

the outer portion may comprise one of a lock protrusion and a lock recess and the housing comprises the other of the lock protrusion and the lock recess, the lock protrusion received by the lock recess to secure the outer portion to the housing, and wherein the lock protrusion is separated from the lock recess before the surface of the removal projection engages the corresponding surface of the rigid needle shield upon axial movement of the outer portion away from the housing.

the drug delivery device may comprise: a housing; a syringe assembly comprising a barrel, a stopper, a cannula, and a rigid needle shield receiving at least a portion of the cannula, at least a portion of the syringe assembly positioned within the housing; a drive assembly configured to move the stopper within the barrel upon actuation of the drive assembly, at least a portion of the drive assembly positioned within the housing; and a cap secured to the housing, the cap comprises an outer portion defining an interior space and a retainer comprising a body with a removal projection, wherein a surface of the removal projection is configured to engage a corresponding surface of the rigid needle shield to remove the rigid needle shield upon axial movement of the outer portion of the cap away from the housing, the surface of the removal projection is disengaged from the corresponding surface of the rigid needle shield when the outer portion is secured to the housing;

the drug delivery device may comprise: a housing; a syringe assembly comprising a barrel, a stopper, a cannula, and a rigid needle shield receiving at least a portion of the cannula, at least a portion of the syringe assembly positioned within the housing; a drive assembly configured to move the stopper within the barrel upon actuation of the drive assembly, at least a portion of the drive assembly positioned within the housing; and a cap secured to the housing, the cap comprises an outer portion defining an interior space and a retainer comprising a body with a removal projection, wherein a portion of the retainer is received within the interior space of the outer portion of the cap, and wherein the retainer is secured to and axially moveable relative to the outer portion, the outer portion comprising a retaining tab received by a retainer opening defined by the body of the retainer, the retaining tab is disengaged from the body of the retainer when the outer portion is secured to the housing, the retaining tab of the outer portion is configured to engage the retainer upon axial movement of the outer portion away from the housing and upon axial movement of the outer portion relative to the retainer;

the drug delivery device may comprise: a housing; a syringe assembly comprising a barrel, a stopper, a cannula, and a rigid needle shield receiving at least a portion of the cannula, at least a portion of the syringe assembly positioned within the housing; a drive assembly configured to move the stopper within the barrel upon actuation of the drive assembly, at least a portion of the drive assembly positioned within the housing; a cap secured to the housing, the cap comprises an outer portion defining an interior space and a retainer comprising a body with a removal projection; and a syringe holder positioned within the housing, the syringe holder receiving the syringe assembly, the syringe holder moveable relative to the housing, wherein the syringe holder is disengaged with the drive assembly when the outer portion is secured to the housing, and wherein the syringe holder is engaged with the drive assembly upon axial movement of the outer portion away from the housing;

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein.

Corresponding reference characters indicate corresponding parts throughout the several views. The exemplifications set out herein illustrate exemplary aspects of the disclosure, and such exemplifications are not to be construed as limiting the scope of the disclosure in any manner.

DETAILED DESCRIPTION

Figure 1A:
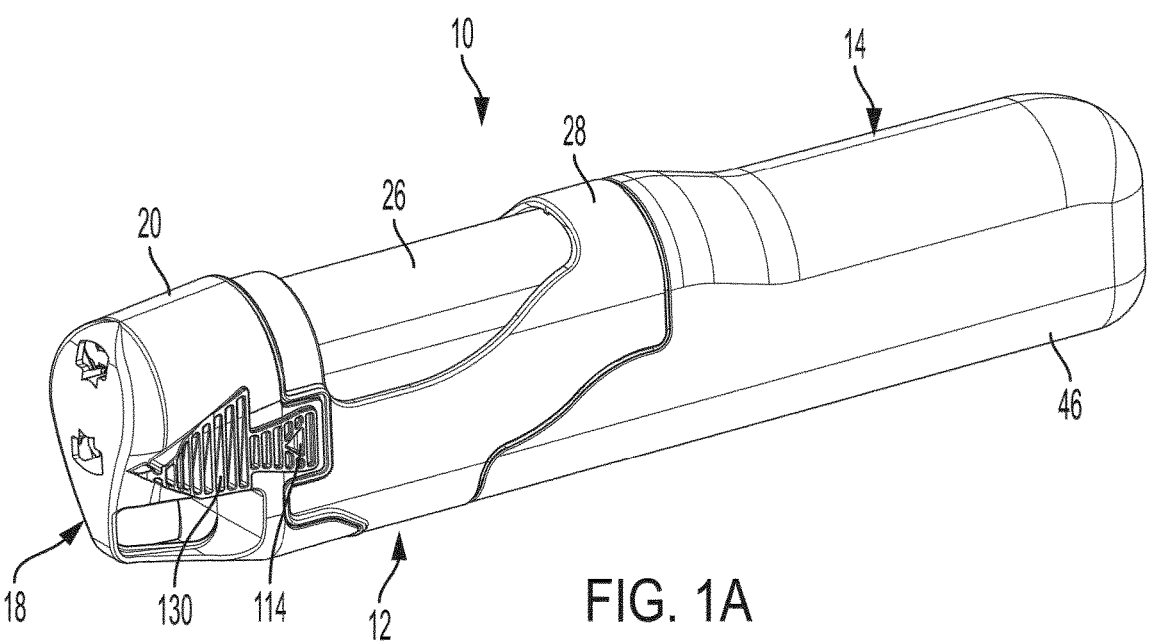
FIG. 1A is a perspective view of a drug delivery device according to one aspect of the present application, showing a storage position of the device.
Figure 1B:
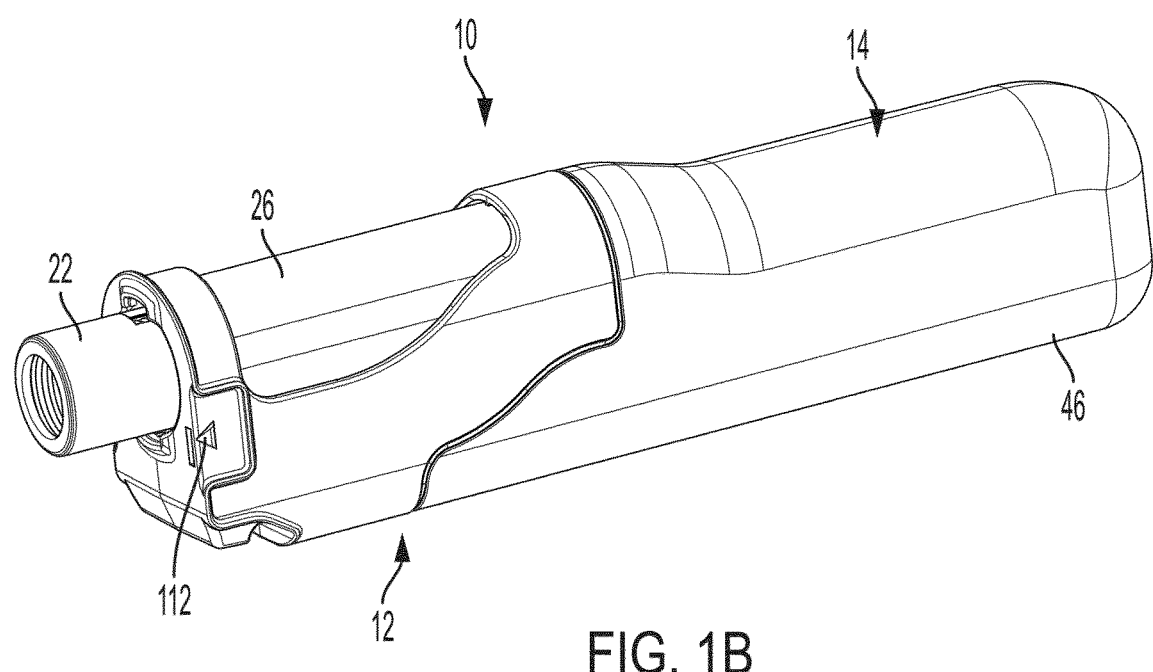
FIG. 1B is a perspective view of the drug delivery device of FIG. 1, showing a pre-use position of the device.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

Referring to FIGS. 1A-10 a drug delivery device 10 according to one aspect of the present invention includes a first subassembly 12, a second subassembly 14, and a syringe assembly 16. The first subassembly 12 includes a cap 18 having an outer portion 20, a needle cover 22, a syringe holder 24, a cassette body 26, and a lower housing shell 28. The second subassembly 14 includes a drive assembly 40, a motor body 42, a lever actuation member 44, and an upper housing shell 46. The syringe assembly 16 is received by the syringe holder 24 and includes a barrel 52, a stopper 54, a cannula 56, and a rigid needle shield (RNS) 58. Although an RNS is utilized, other suitable needle shield arrangements may be utilized. The lower housing shell 28, the cassette body 26, and the upper housing shell 46 generally form a housing for receiving the various components of the device 10, although other suitable housing arrangements may be utilized. As discussed in more detail below, the first subassembly 12 and the second subassembly 14 are secured to each other during assembly by a locking clip 64, although other suitable arrangements may be utilized. The drug delivery device 10 may be an auto-injector, although the features described herein may be incorporated into other suitable drug delivery devices.

Figure 7:
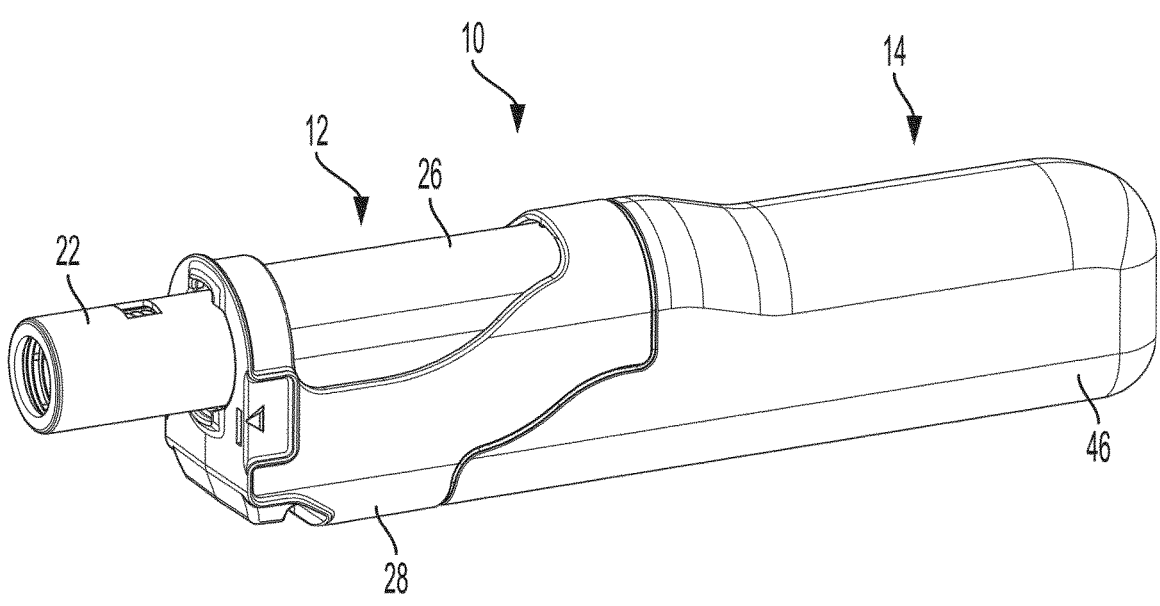
FIG. 7 is a perspective view of the drug delivery device of FIG. 1, showing a post-use position of the device.
Figure 8:
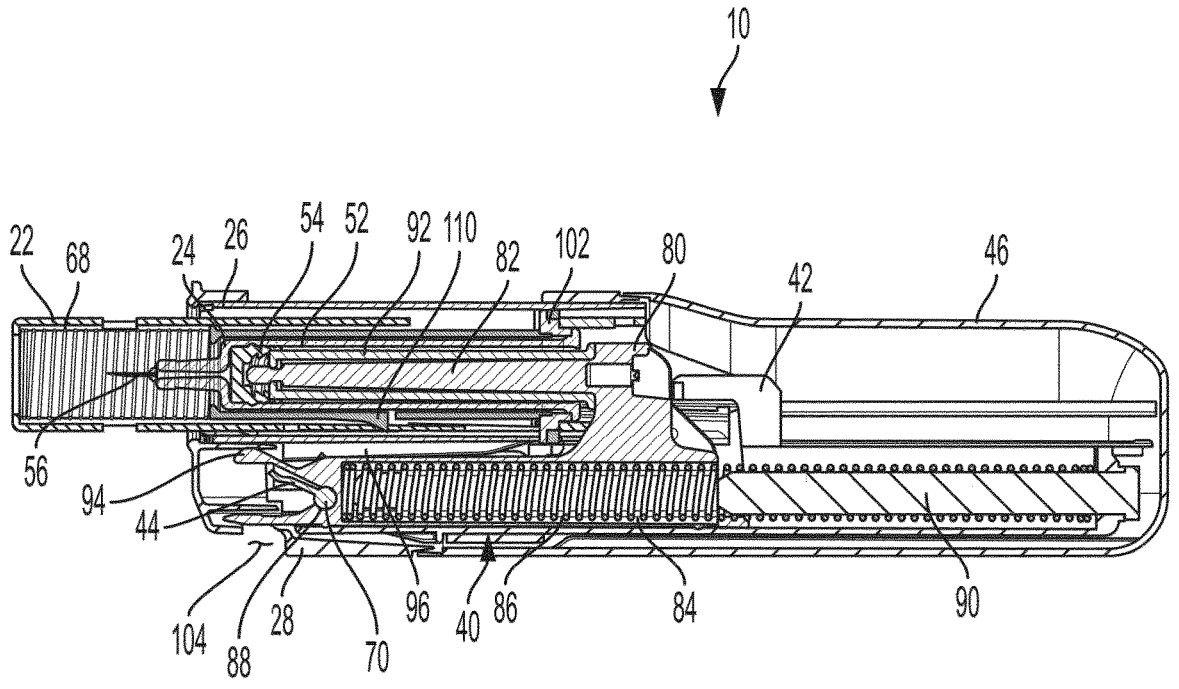
FIG. 8 is a cross-sectional view of the drug delivery device of FIG. 1, showing a post-use position of the device.
Figure 9:
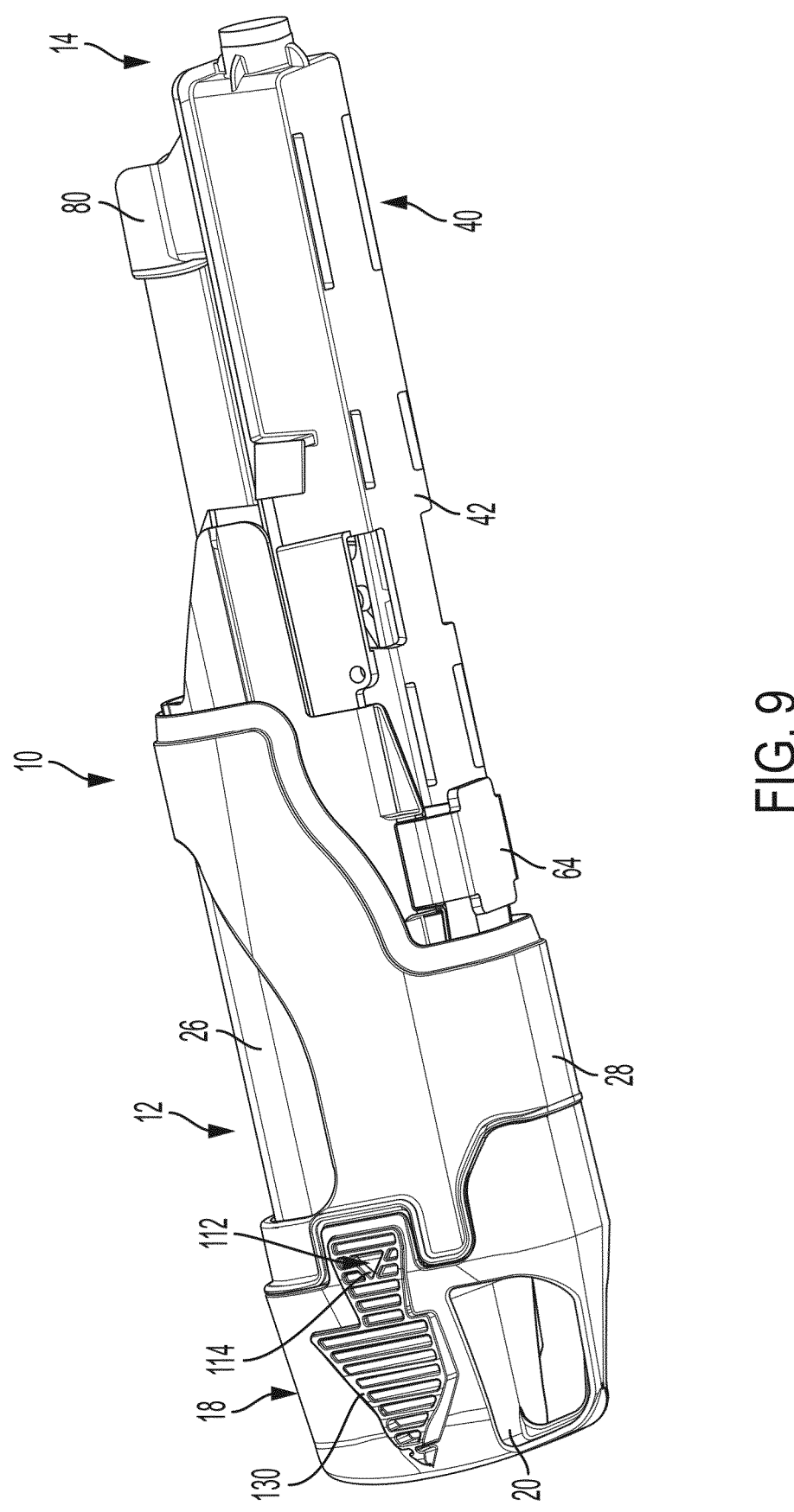
FIG. 9 is a perspective view of the drug delivery device of FIG. 1, showing a locking clip.
Figure 10:
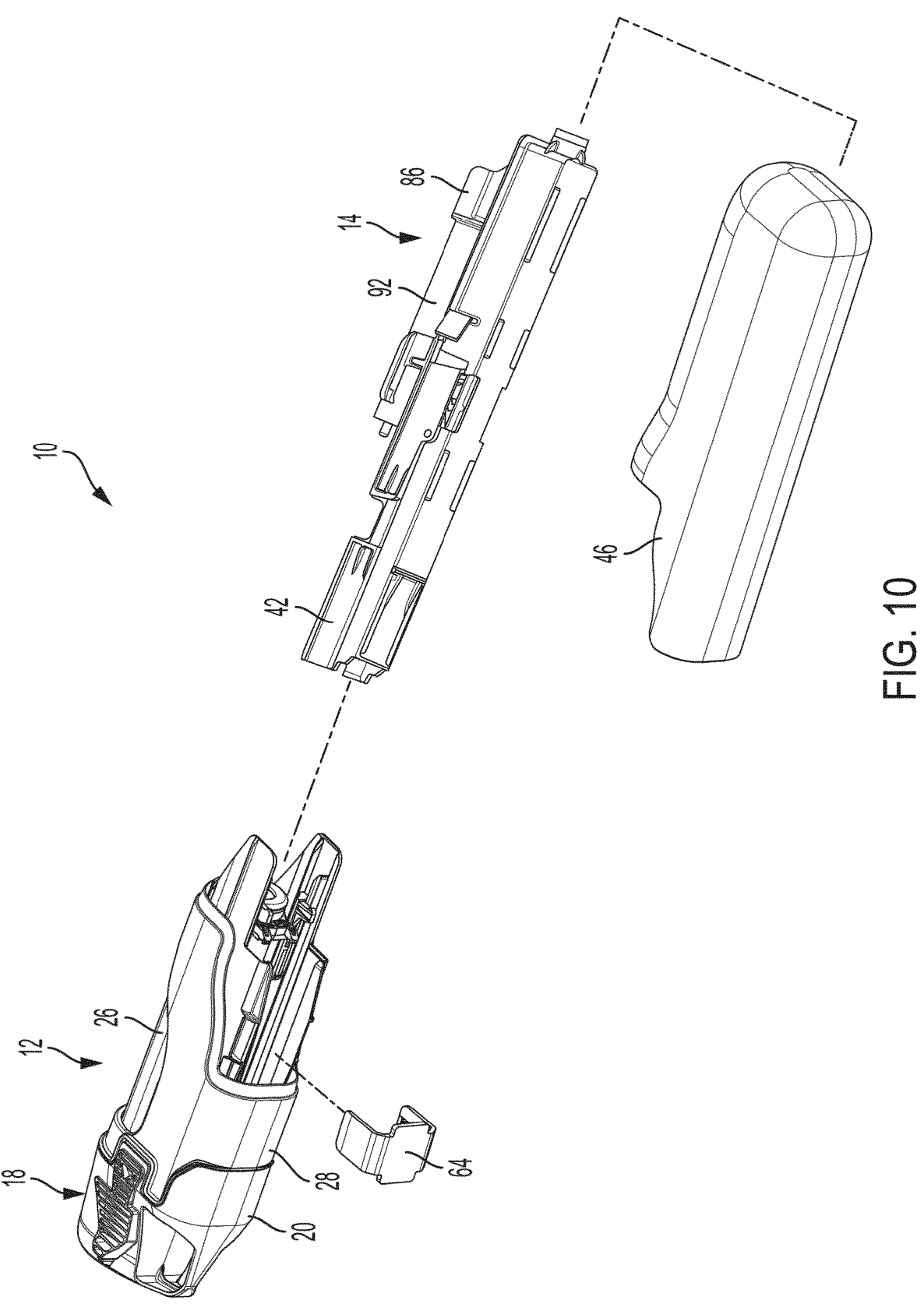
FIG. 10 is an exploded perspective view of the drug delivery device of FIG. 1, showing a locking clip.
Figure 11A:
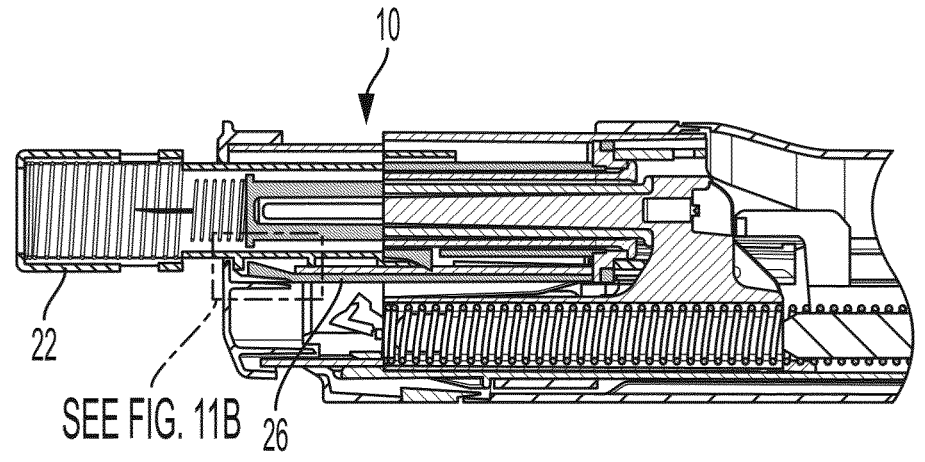
FIG. 11A is a partial cross-sectional view of the drug delivery device of FIG. 1, showing a lock arm of a cassette body.
Figure 11B:
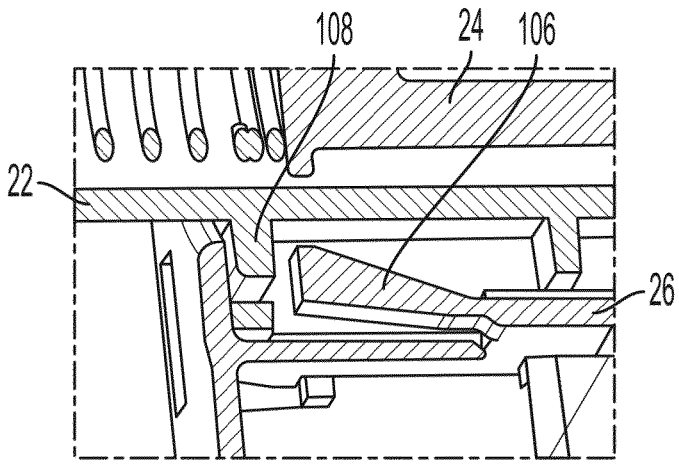
FIG. 11B is an enlarged cross-sectional view of the area indicated in FIG. 11A.

The drug delivery device 10 is configured to automatically deliver a dose of medicament from the syringe assembly 16 to a patient upon actuation of the device 10. More specifically, upon actuation of the drug delivery device 10, the drive assembly 40 is configured to engage the stopper 54 of the syringe assembly 16, displace the syringe assembly 16 such that the cannula 56 pierces the skin of the patient, and displace the stopper 54 within the barrel 52 of the syringe assembly 16 to deliver the medicament within the barrel 52. The drug delivery device 10 includes a storage position (FIGS. 1A and 2A), a pre-use position (FIGS. 1B and 2B), an actuation position (FIGS. 3 and 4), an injection position (FIGS. 5 and 6), and a post-use position (FIGS. 7 and 8). As discussed in more detail below, the needle cover 22 is configured to shield the cannula 56 of the syringe assembly 16 from the patient when the device 10 is in the pre-use and the post-use positions. In particular, the needle cover 22 is moveable between a pre-use position, an actuation position, and a post-use positon, with a spring 68 biasing the needle cover 22 towards the pre-use position and the post-use position. The spring 68 is positioned between the needle cover 22 and the syringe holder 24, although other suitable arrangements may be utilized. The lever actuation member 44 is moveable between a locked position where movement of the drive assembly 40 is prevented and a released position where movement of the drive assembly 40 is allowed. More specifically, the lever actuation member 44 is rotatable about a rotation axis 70 between the locked position and the released position. When the lever actuation member 44 is in the locked position, the lever actuation member 44 is engaged with the motor body 42 and the drive assembly 40 to prevent movement of the drive assembly 40. When the lever actuation member 44 is in the released position, the lever actuation member 44 is disengaged from the motor body 42 thereby allowing movement of the drive assembly 40 toward the syringe assembly 16. The rotation axis 70 of the lever actuation member 44 extends perpendicular to a longitudinal axis of the device 10, although other suitable arrangements may be utilized.

Referring again to FIGS. 1-10, the drive assembly 40 includes a plunger body 80 having a plunger rod portion 82 and a drive member 84. The drive member 84 is a compression spring received within a drive opening 86 defined by the plunger body 80, although other suitable drive members may be utilized, including, but not limited to, compressed gas, an electric motor, hydraulic pressure, other types of springs, etc. The drive member 84 engages the plunger body 80 and the motor body 42 and biases the plunger body 80 in a direction extending from the second subassembly 14 toward the first subassembly 12. The plunger body 80 defines a lever opening 88 that receives the lever actuation member 44 and defines the rotation axis 70 of the lever actuation member 44. The lever actuation member 44 prevents movement of the plunger body 80 when the lever actuation member 44 is in the locked position through engagement of the lever actuation member 44 with the motor body 42. Upon rotation of the lever actuation member 44 from the locked position to the released position, the lever actuation member 44 is disengaged from the motor body 42 thereby allowing the drive member 84 to move the plunger body 80 and the plunger rod portion 82 toward the first subassembly 12. The plunger rod portion 82 and the drive member 84 are spaced from and parallel to each other and extend in a longitudinal direction of the device 10.

The drive assembly 40 further includes a spring guide member 90 secured to the upper housing shell 46 and received within the drive opening 86 of the plunger body 80. The drive member 84 is received by the spring guide member 90 such that the drive member 84 is positioned between the plunger body 80 and the spring guide member 90. The drive assembly 40 also includes a plunger rod cover 92 that receives the plunger rod portion 82 of the plunger body 80. The plunger rod cover 92 is configured to guide insertion of the plunger rod portion 82 into the barrel 52 of the syringe assembly 16 and engage the stopper 54 of the syringe assembly 16 to dispense the medicament from the barrel 52 of the syringe assembly 16. The plunger rod cover 92 and the plunger rod portion 82 may be formed integrally or formed as separate components.

The plunger body 80 of the drive assembly 40 also includes an audio indicator member 94 configured to provide an audible indication to a user when the device 10 transitions to the post-use position. As discussed in more detail below, the audio indicator member 94 is configured to engage one or more ribs 96 of the cassette body 26 when the device 10 is in the injection position thereby deflecting the audio indicator member 94. When the drug delivery device 10 transitions from the injection position to the post-use position, the audio indicator member 94 disengages from the rib(s) 96 of the cassette body 26 and contacts the lower housing shell 28 to provide an audible click, although the audio indicator member 94 could also contact other suitable portions of the device 10 to provide the audible indicator.

Figure 2A:
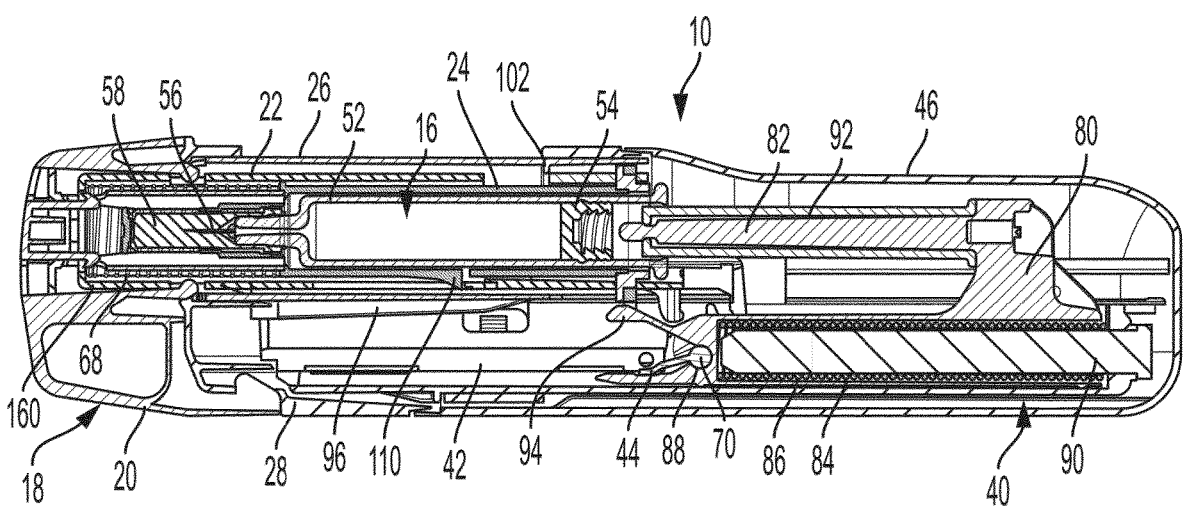
FIG. 2A is a cross-sectional view of the drug delivery device of FIG. 1, showing a storage position of the device.
Figure 2B:
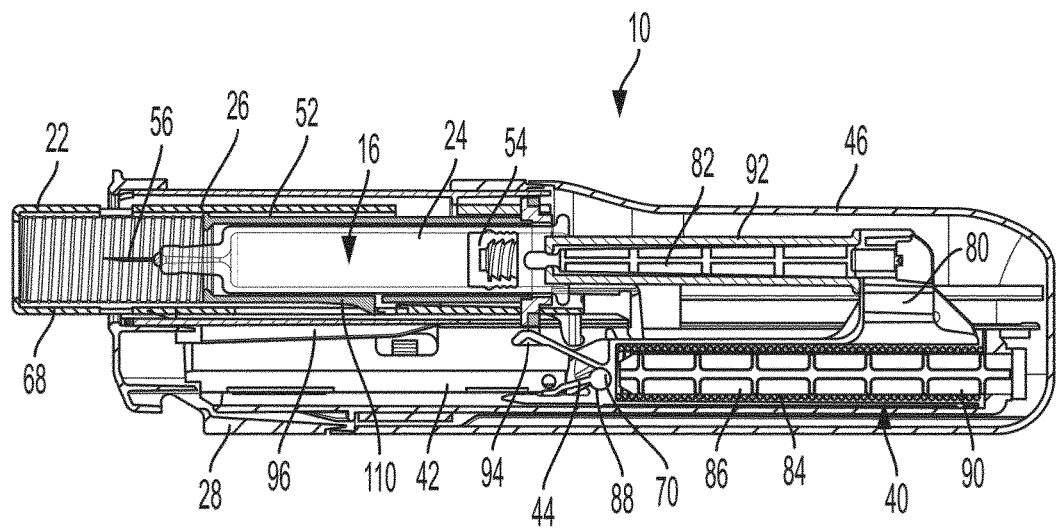
FIG. 2B is a cross-sectional view of the drug delivery device of FIG. 1, showing a pre-use position of the device.

Referring to FIGS. 1A-2B, in the storage position, the cap 18 is secured to the lower housing shell 28 and engaged with the needle cover 22. Movement of the needle cover 22 from the pre-use position to the actuation position causes engagement between the needle cover 22 and the lever actuation member 44 thereby actuating the drive assembly 40. After removal of the cap 18 by grasping the outer portion 20, the needle cover 22 may be moved from the pre-use position to the actuation position by pressing the needle cover 22 against a skin surface of a patient and axially pressing the device 10 against the skin surface. As detailed below, the engagement between the cap 18 and the needle cover 22 prevents the needle cover 22 from moving into engagement with the lever actuation member 44. Accordingly, removal of the cap 18 from the device 10 allows for the actuation of the device 10. As discussed in more detail below, removal of the cap 18 from the device 10, as shown in FIGS. 1B and 2B, also removes the RNS 58 from the syringe barrel 52 thereby exposing the cannula 56, which is still received within the needle cover 22 in the pre-use position of the device 10.

Figure 3:
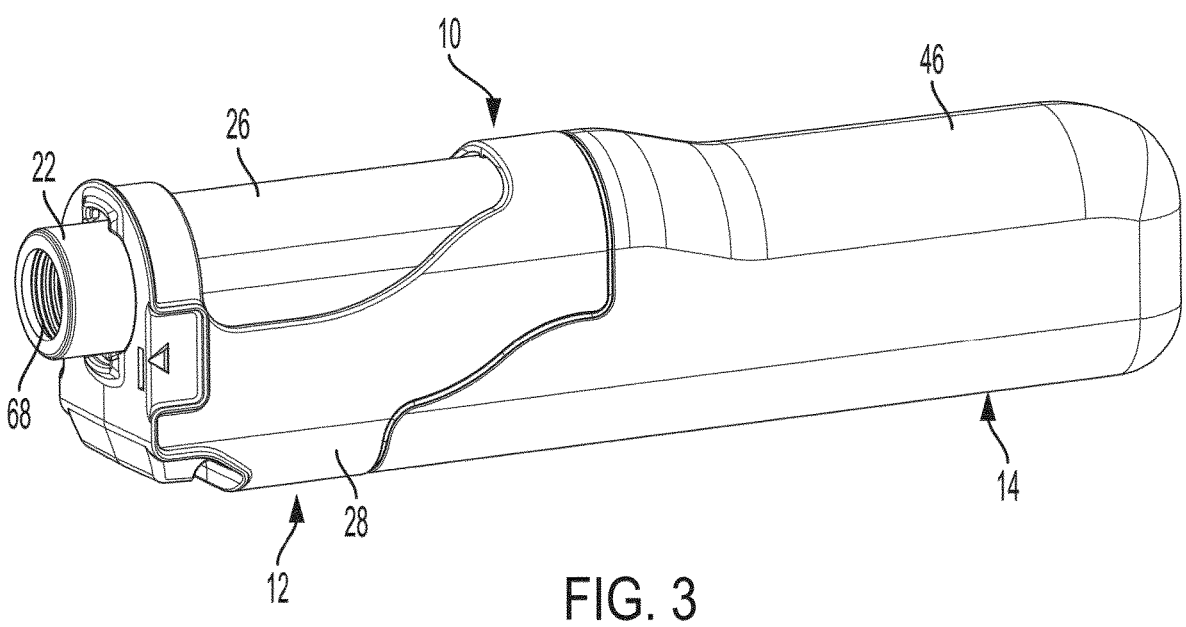
FIG. 3 is a perspective view of the drug delivery device of FIG. 1, showing an actuation position of the device.
Figure 4:
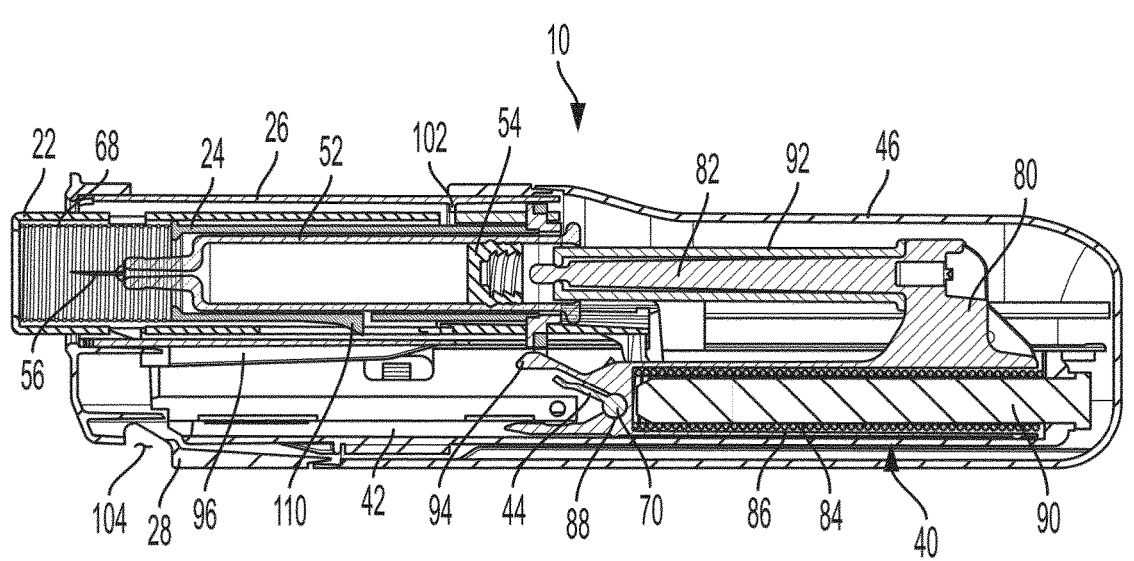
FIG. 4 is a cross-sectional view of the drug delivery device of FIG. 1, showing an actuation position of the device.

Referring to FIGS. 3 and 4, in the actuation position, the cap 18 is removed and the needle cover 22 is positioned in the actuation position by engaging a skin surface of a patient, which moves the needle cover 22 further within the device 10 toward the second subassembly 14. When the needle cover 22 has moved a sufficient distance within the device 10, a portion of the needle cover 22 engages the lever actuation member 44, which rotates the lever actuation member 44 about the rotation axis 70 from the locked position to the released position.

Figure 5:
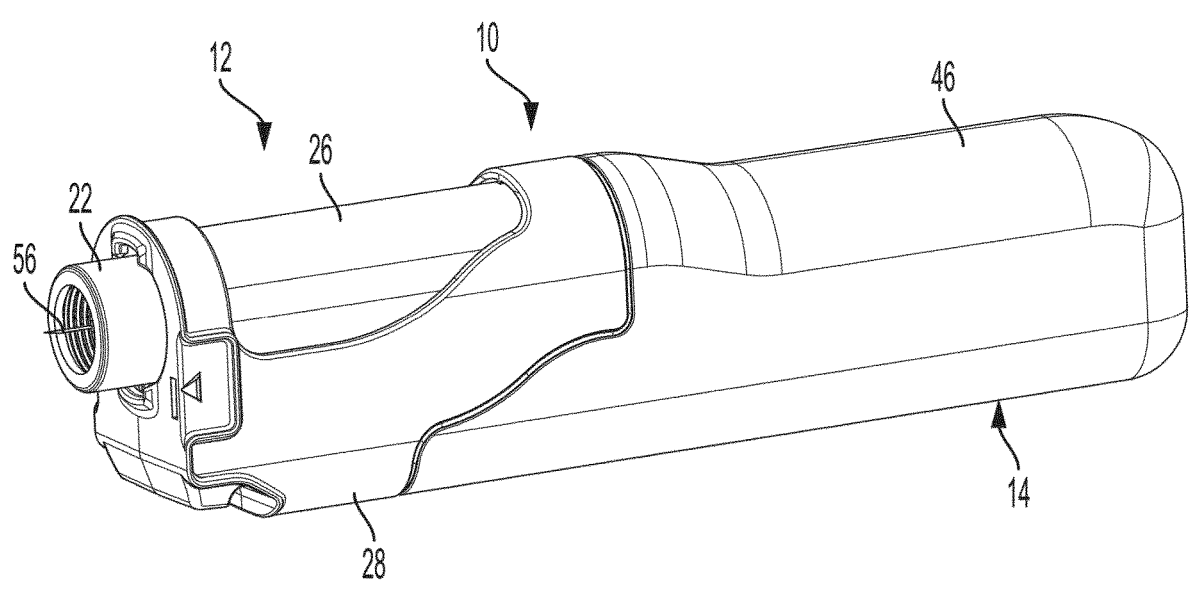
FIG. 5 is a perspective view of the drug delivery device of FIG. 1, showing an injection position of the device.
Figure 6:
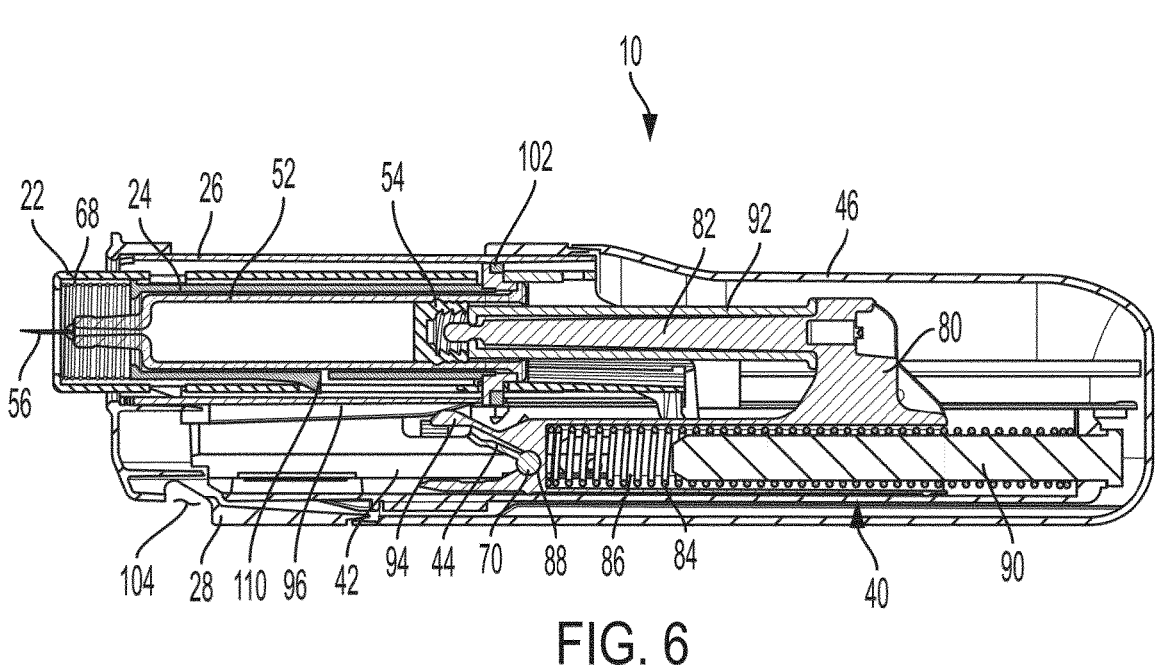
FIG. 6 is a cross-sectional view of the drug delivery device of FIG. 1, showing an injection position of the device.

Referring to FIGS. 5 and 6, in the injection position, the lever actuation member 44 is in the released position, which allows the plunger body 80 of the drive assembly 40 to move toward the first subassembly 12 such that the plunger body 80 or the plunger rod cover 92 engages the stopper of the syringe assembly 16. Initial engagement of the drive assembly 40 with the syringe assembly 16 moves the syringe assembly 16 and the syringe holder 24 within the device 10 and relative to the cassette body 26 until the syringe holder 24 abuts a stop 102 defined by the cassette body 26. During this initial movement of the syringe assembly 16 and syringe holder 24 with the needle cover 22 pressed against a skin surface of a patient, the cannula 56 of the syringe assembly 16 extends beyond the needle cover 22 and pierces the skin surface of the patient. Further movement of the plunger body 80, which is driven by the drive member 84, moves the stopper 54 relative to the barrel 52 of the syringe assembly 16 to dispense medicament from the barrel 52 of the syringe assembly 16, through the cannula 56, and into the patient.

The plunger body 80 will continue moving until the stopper 54 bottoms out on the barrel 52 of the syringe assembly 16. When the stopper 54 bottoms out or just before the stopper 54 bottoms out, the audio indicator member 94 will disengage from the rib(s) 96 of the cassette body 26 and contact the lower housing shell 28 at approximately the same time to provide the audible indication to the patient that the dose of medicament has been delivered. In addition to the audible indication, the drug delivery device 10 provides one or more visual indicators to notify a patient of the status of the device 10. In particular, the cassette body 26 may be formed from transparent material to allow visual confirmation of movement of the stopper 54 and/or another visual indicator provided by the drive assembly 40, syringe holder 24, and/or syringe assembly 16. The lower housing shell 28 also defines an indicator opening 104, which provides visual indication that the plunger body 80 is in a final position and the dose of medicament has been delivered. The visual indicators may utilize contrasting colors, symbols, patterns, or any other suitable visual indicia to indicate the various statuses of the device.

Figure 12:
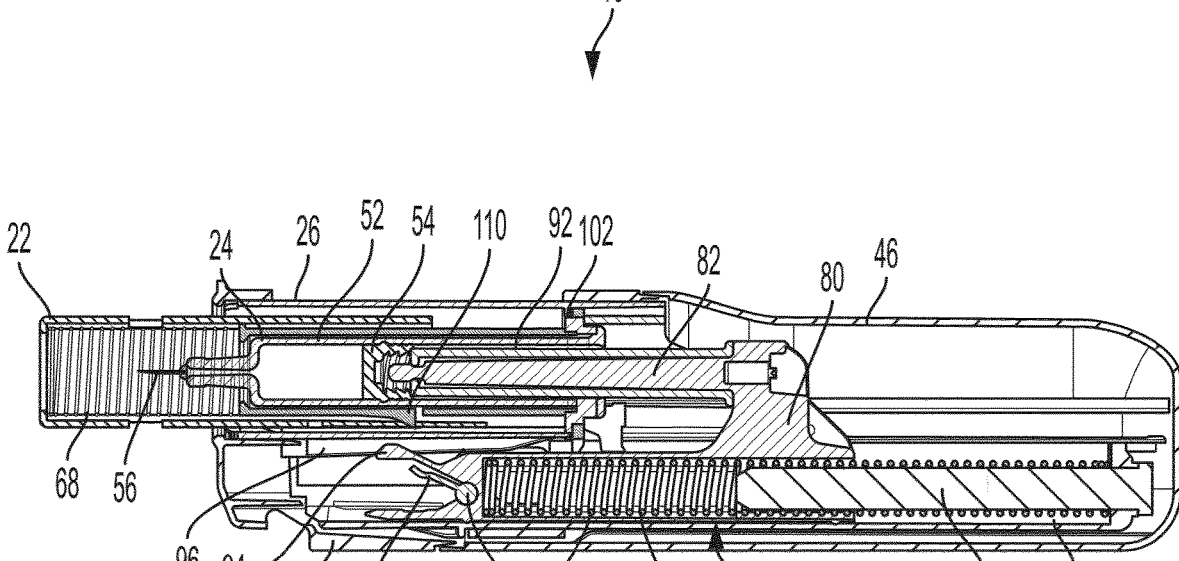
FIG. 12 is a cross-sectional view of the drug delivery device of FIG. 1, showing a post-use position of the device prior to full delivery of medicament.

Referring to FIGS. 7, 8, 11A, 11B, and 12, in the post-use position, the needle cover 22 extends to the post-use position to shield the cannula 56 when the needle cover 22 is removed from a skin surface of a patient. As shown more clearly in FIG. 11B, the cassette body 26 includes at least one lock arm 106 and the needle cover 22 includes at least one lock protrusion 108, although other suitable configurations may be utilized. The lock arm 106 of the cassette body 26 engages the lock protrusion 108 of the needle cover 22 to prevent any further use of the device 10 and exposing of the cannula 56 of the syringe assembly 16. During the transition of the device 10 from the injection position to the post-use position, the lock arm 106 of the cassette body 26 deflects to allow the lock protrusion 108 of the needle cover 22 to pass by the cassette body 26 with the lock arm 106 returning to its original position to prevent movement of the needle cover 22 back toward the pre-use and actuation positions. In the pre-use position of the needle cover 22, a portion of the needle cover 22 engages a cover stop 110 of the syringe holder 24 to limit axial movement of the needle cover 22 in a direction extending from the second subassembly 14 toward the first subassembly 12. After use of the device 10, the syringe holder 24 is displaced within the cassette body 26 relative to the needle cover 22, which allows the needle cover 22 to extend to the post-use position when a patient removes the needle cover 22 from a skin surface. As shown in FIG. 12, the needle cover 22 will move to the post-use position when the needle cover 22 is removed from a skin surface of a patient regardless of a position of the stopper 54 within the barrel 52 of the syringe assembly 16. Accordingly, if a patient removes the needle cover 22 from a skin surface after only a portion of the dose of medicament has been delivered, the needle cover 22 will still move to the post-use position and will prevent further use of the device 10.

Referring to FIGS. 1A, 1B, and 13A-15C, as discussed above, engagement between the cap 18 and the needle cover 22 prevents the needle cover 22 from moving into engagement with the lever actuation member 44. The cannula 56 is positioned within the needle cover 22 when the needle cover 22 is in the pre-use position and the post-use position. The needle cover 22 is configured to actuate the drive assembly 40 when the needle cover 22 is in the actuation position. Removal of the cap 18 from the device 10 allows for the actuation of the device 10. More precisely, in one aspect of the present application, the outer portion 20 of the cap 18 includes a body 116 defining an interior space 118 that receives a portion of the needle cover 22 when the device 10 is in the storage position with the outer portion 20 secured to the lower housing shell 28. The outer portion 20 of the cap 18 is secured to the lower housing shell 28 via a lock protrusion 112 that is received by a lock recess 114 defined by the body 116 of the outer portion 20 of the cap 18. The outer portion 20 also includes a grip surface 130 to facilitate the grasping and removal of the outer portion 20 of the cap 18 from the lower housing shell 28.

Figure 13A:
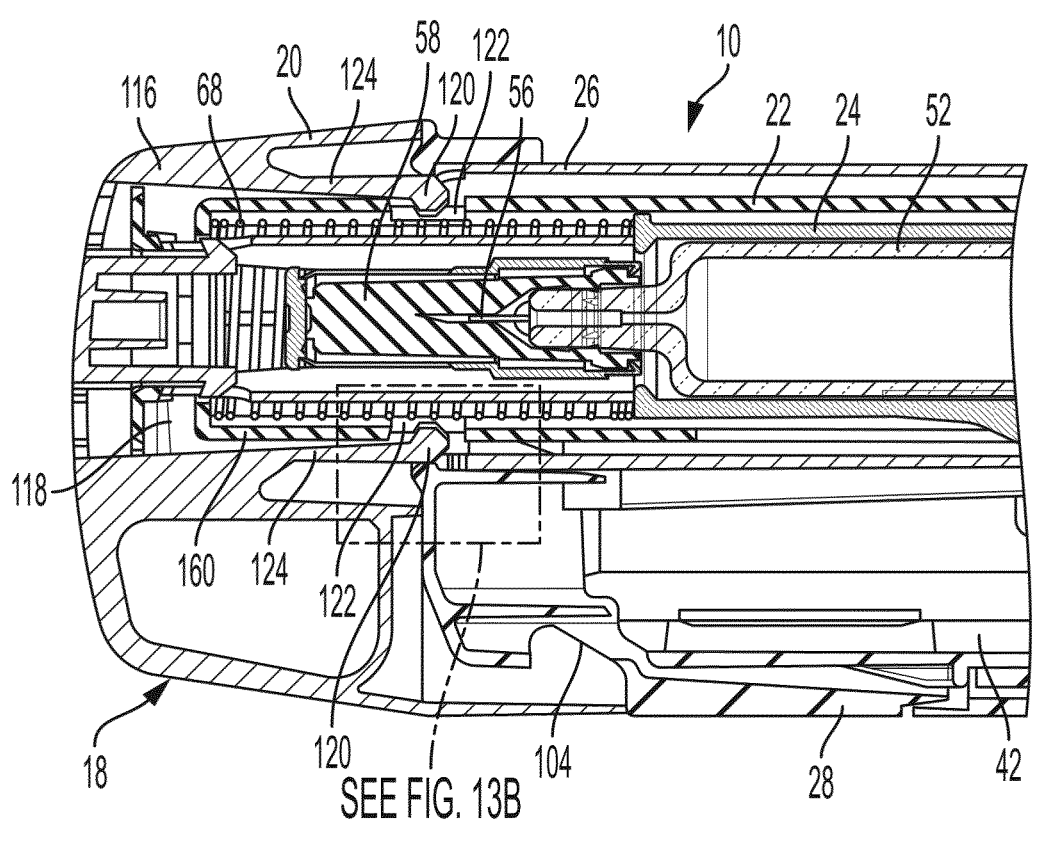
FIG. 13A is a partial cross-sectional view of the drug delivery device of FIG. 1, showing a cap of the device.
Figure 13B:
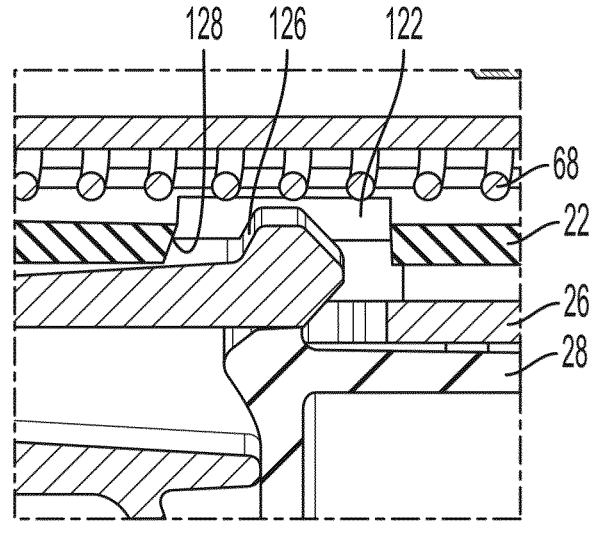
FIG. 13B is an enlarged cross-sectional view of the area indicated in FIG. 13A.

The outer portion 20 includes a pair of protrusions 120 received by cap openings 122 defined by the needle cover 22, although one or more protrusions 120 and one or more cap openings 122 may be utilized. The protrusions 120 of the outer portion 20 are configured to engage the needle cover 22 upon movement of the needle cover 22 from the pre-use position to the actuation position. For instance, with the device 10 in the storage position with the outer portion 20 secured to the lower housing shell 28, if the device 10 is dropped or impacted to apply a force to the needle cover 22, the lever actuation member 44, and/or other component, the protrusions 120 of the outer portion 20 restrict movement of the needle cover 22, which prevents any unintended actuation of the device 10. The protrusions 120 of the outer portion 20 are moveable in a radial direction via extension arms 124 of the outer portion 20. As shown in FIG. 13B, for example, engagement between the extension arms 124 and the lower housing shell 28 prevents radially outward movement of the protrusions 120. More precisely, the lower housing shell 28 includes a skirt configured to surround the extension arms 124 of the outer portion 20 when the outer portion 20 is mounted on the lower housing shell 28, which prevents radially outward movement of the protrusions 120 as long as the outer portion 20 is mounted on the lower housing shell 28. The protrusions 120 are configured to be removed from the cap opening 122 of the needle cover 122 upon axial movement of the outer portion 20. In particular, the protrusions 120 are configured to engage the needle cover 22 and deflect radially outward upon axial movement of the outer portion 20 of the cap 18.

Referring to FIG. 13B, the protrusions 120 each define a first cam surface 126 and the needle cover 22 defines a second cam surface 128, with the first cam surface 126 configured to engage the second cam surface 128 to deflect each protrusion 120 radially outward, which allows separation of the outer portion 20 from the needle cover 22. The first and second cam surfaces 126,128 are complementary, inclined surfaces, although other suitable arrangements may be utilized.

Figure 14:
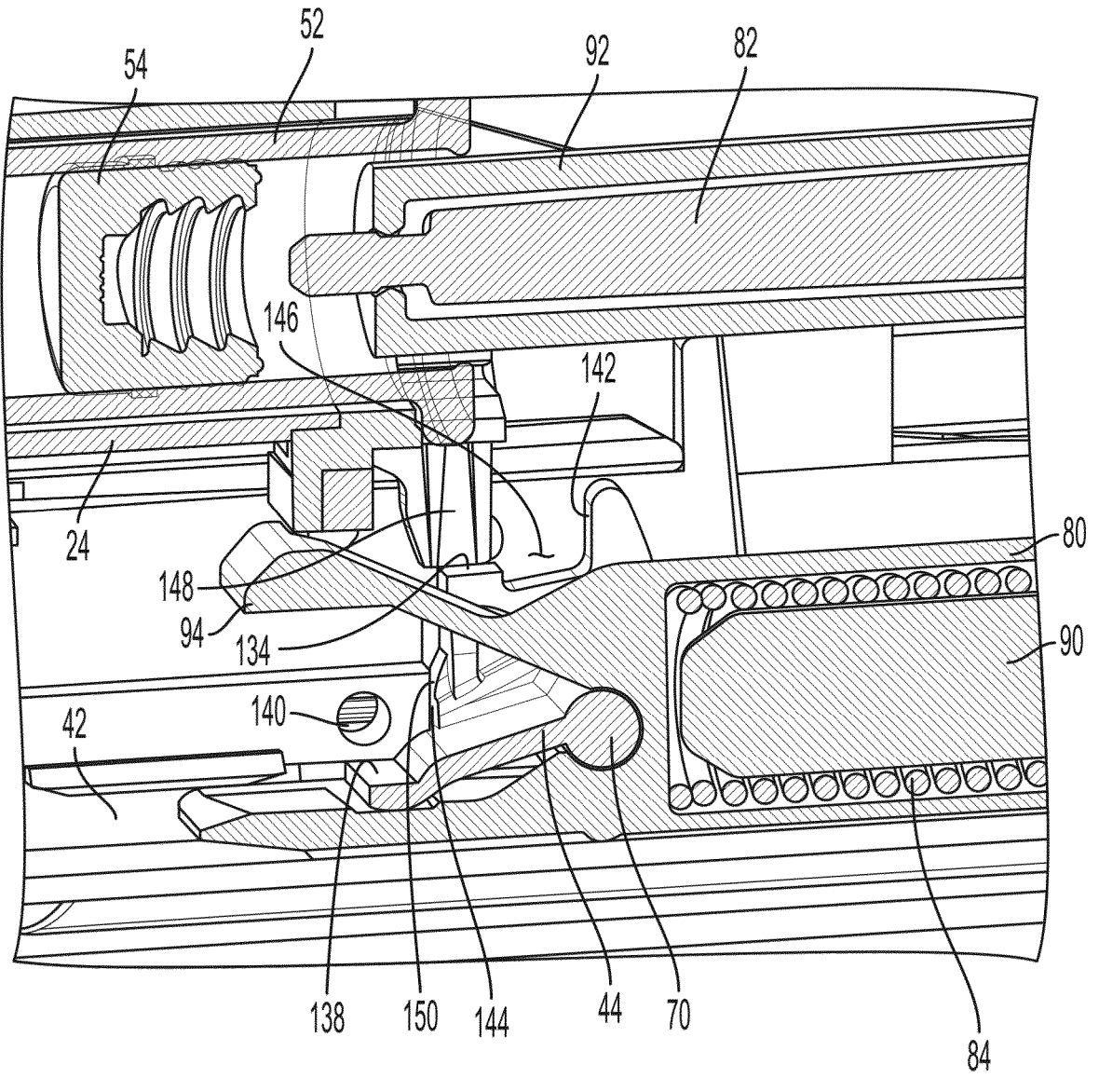
FIG. 14 is a partial cross-sectional view of the drug delivery device of FIG. 1, showing a lever actuation member with the device in a storage position.
Figures 15A, 15B, 15C:
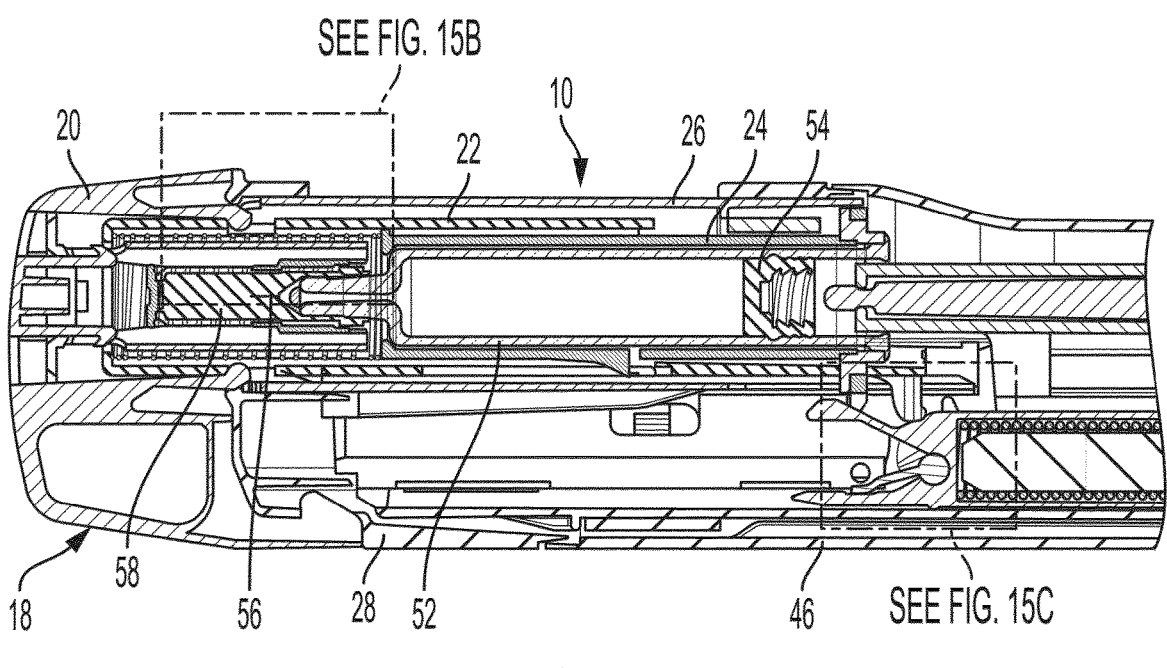
FIG. 15A is a partial cross-sectional view of the drug delivery device of FIG. 1, showing a storage position of the device and movement of a needle cover.
FIG. 15B is an enlarged cross-sectional view of the area indicated in FIG. 15A.
FIG. 15C is an enlarged cross-sectional view of the area indicated in FIG. 15A.
Figure 16:
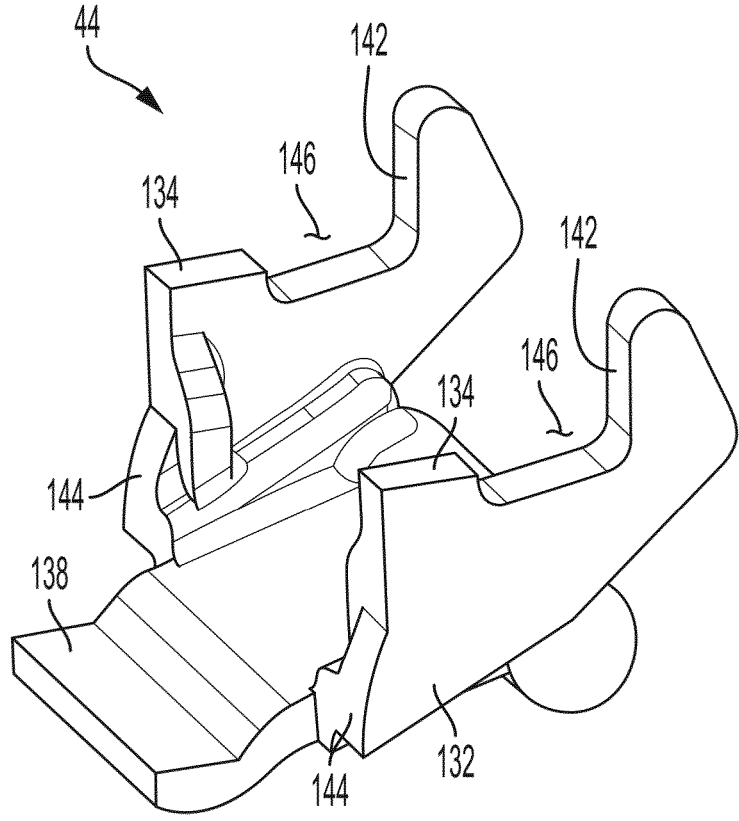
FIG. 16 is a perspective view of a lever actuation member according to one aspect of the present application.

Referring to FIGS. 14-16, the needle cover 22 prevents movement or rotation of the lever actuation member 44 from the locked position to the released position when the needle cover 22 is in the pre-use position. The lever actuation member 44 includes a body 132 having a restriction surface 134 configured to engage the needle cover 22 and restrict rotation of the lever actuation member 44 when the needle cover 22 is in the pre-use position. When the device 10 is in the storage position, if the device 10 is dropped or impacted to apply a force to the lever actuation member 44, the lever actuation member 44 is prevented from fully rotating to allow actuation of the drive assembly 40 due to the engagement between the restriction surface 134 of the lever actuation member 44 and the needle cover 22. The restriction surface 134 is spaced from the needle cover 22 to form a gap 136 when the device 10 is in the storage and pre-use positions to prevent any increase in friction in the movement of the needle cover 22 while still preventing unintended actuation of the device 10.

The body 132 of the lever actuation member also includes an assembly surface 138 configured to engage a locking pin (not shown) received by a pin opening 140 defined by the motor body 42. Prior to assembly, the second subassembly 14 may include a locking pin that extends through the pin opening 140, which prevents rotation of the lever actuation member 44 and unintentional actuation of the drive assembly 40 during assembly of the device 10. The body 132 of the lever actuation member also includes a needle cover contact surface 142, a motor body contact surface 144, and defines a recessed area 146. The needle cover contact surface 142 of the lever actuation member 44 engages a lever contact portion 148 of the needle cover 22 when the needle cover 22 is moved to the actuation position thereby rotating the lever actuation member 44 from the locked position to the released position. The motor body contact surface 144 of the lever actuation member 44 engages a stop surface 150 of the motor body 42 when the lever actuation member 44 is in the locked position, which prevents movement of the plunger body 80. When the lever actuation member 44 rotates from the locked position to the released position, the motor body contact surface 144 disengages from the stop surface 150 of the motor body 42, which allows the drive member 84 to move the plunger body 80.

The recessed area 146 of the lever actuation member 44 provides clearance for the lever contact portion 148 of the needle cover 22 to allow for rotation of the lever actuation member 44 from the locked position to the released position. The position of the restriction surface 134 of the lever actuation member 44 overlaps in an axial direction of the device 10 with the position of the lever contact portion 148 of the needle cover 22 when the needle cover 22 is in the pre-use position and until the needle cover 22 has fully moved to the actuation position, which prevents unintentional actuation of the device 10 as discussed above. When the needle cover 22 is fully moved to the actuation position, the lever contact portion 148 of the needle cover 22 no longer overlaps with the position of the restriction surface 134 of the lever actuation member and, instead, overlaps with the position of the recessed area 146 in a direction extending in an axial direction of the device 10 and engages the needle cover contact surface 142 to rotate the lever actuation member 44 as described above. The restriction surface 134 of the lever actuation member 44 is planar and is configured to engage a corresponding planar surface on the bottom of the needle cover contact surface 142 when the needle cover 22 is in the pre-use position, although other suitable configurations may be utilized.

Referring to FIGS. 17A-24, according to one aspect of the present application, the device further includes a retainer 160 having a body 162 with a removal projection 164 configured to remove the RNS 58 upon axial movement of the outer portion 20 of the cap 18 away from the lower housing shell 28. A portion of the retainer 160 is received within the interior space 118 of the outer portion 20. The outer portion 20 includes a retaining tab 166 received by a retainer opening 168 defined by the body 162 of the retainer 160 to secure the retainer 160 to the outer portion 20. As detailed below, the retaining tab 166 is configured to engage the retainer 160 upon axial movement of the outer portion 20 away from the lower housing shell 28. As shown more clearly in FIGS. 23 and 24, the retainer 160 further includes a pair of wings 170 extending radially outward from the body 162 of the retainer 160, with each wing 170 configured to engage a rib 172 extending radially inward from the body 162 of the outer portion 20. The wings 170 prevent wobbling between the outer portion 20 and the retainer 160 once the outer portion 20, the retainer 160, and the RNS 58 has been removed.

Figures 17A, 17B, 17C, 17D, 17E, 17F:
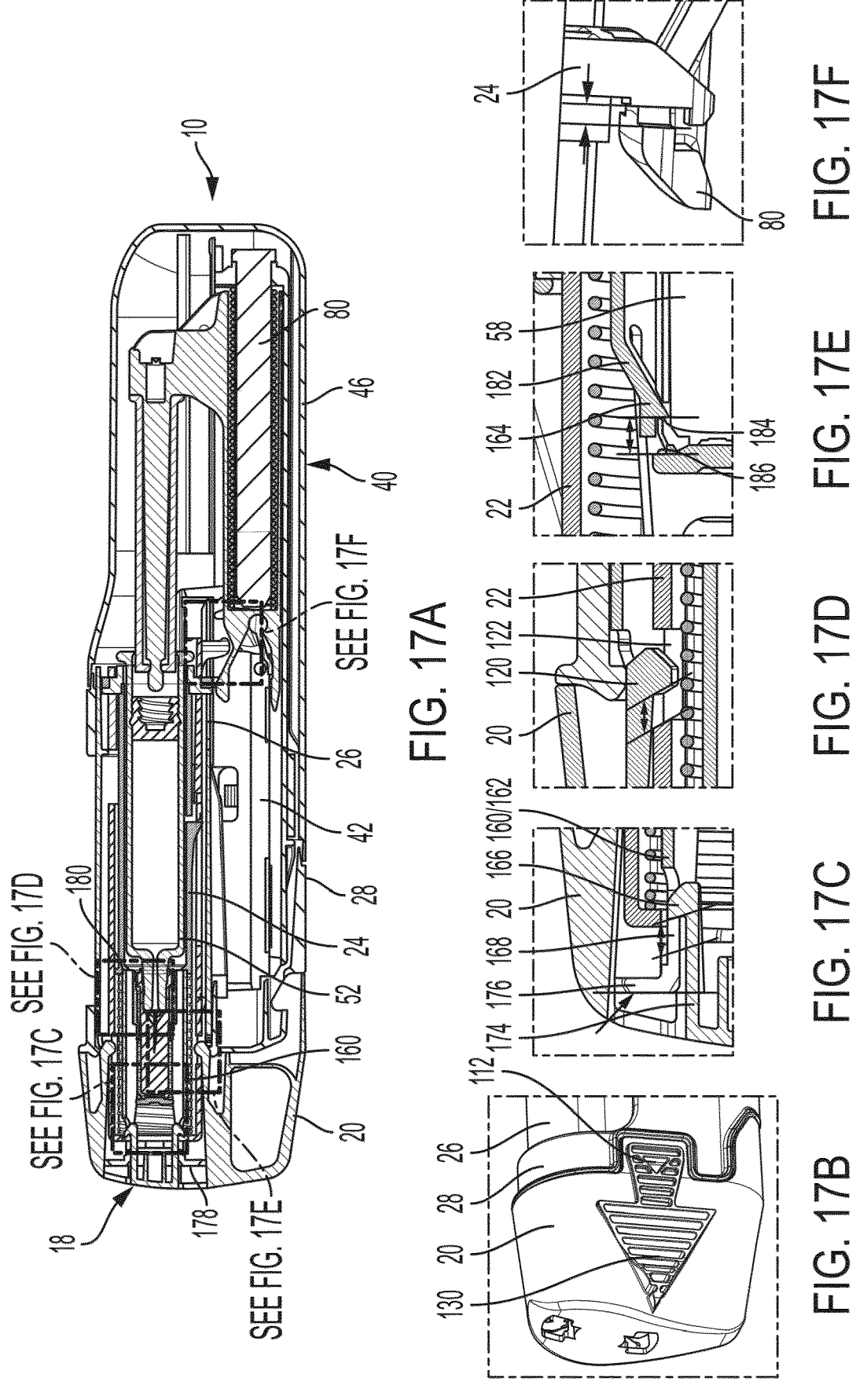
FIG. 17A is a cross-sectional view of the drug delivery device of FIG. 1, showing a storage position of the device.
FIG. 17B is an enlarged cross-sectional view of the area indicated in FIG. 17A.
FIG. 17C is an enlarged cross-sectional view of the area indicated in FIG. 17A.
FIG. 17D is an enlarged cross-sectional view of the area indicated in FIG. 17A.
FIG. 17E is an enlarged cross-sectional view of the area indicated in FIG. 17A.
FIG. 17F is an enlarged cross-sectional view of the area indicated in FIG. 17A.
Figures 20A, 20B, 20C, 20D, 20E, 20F:
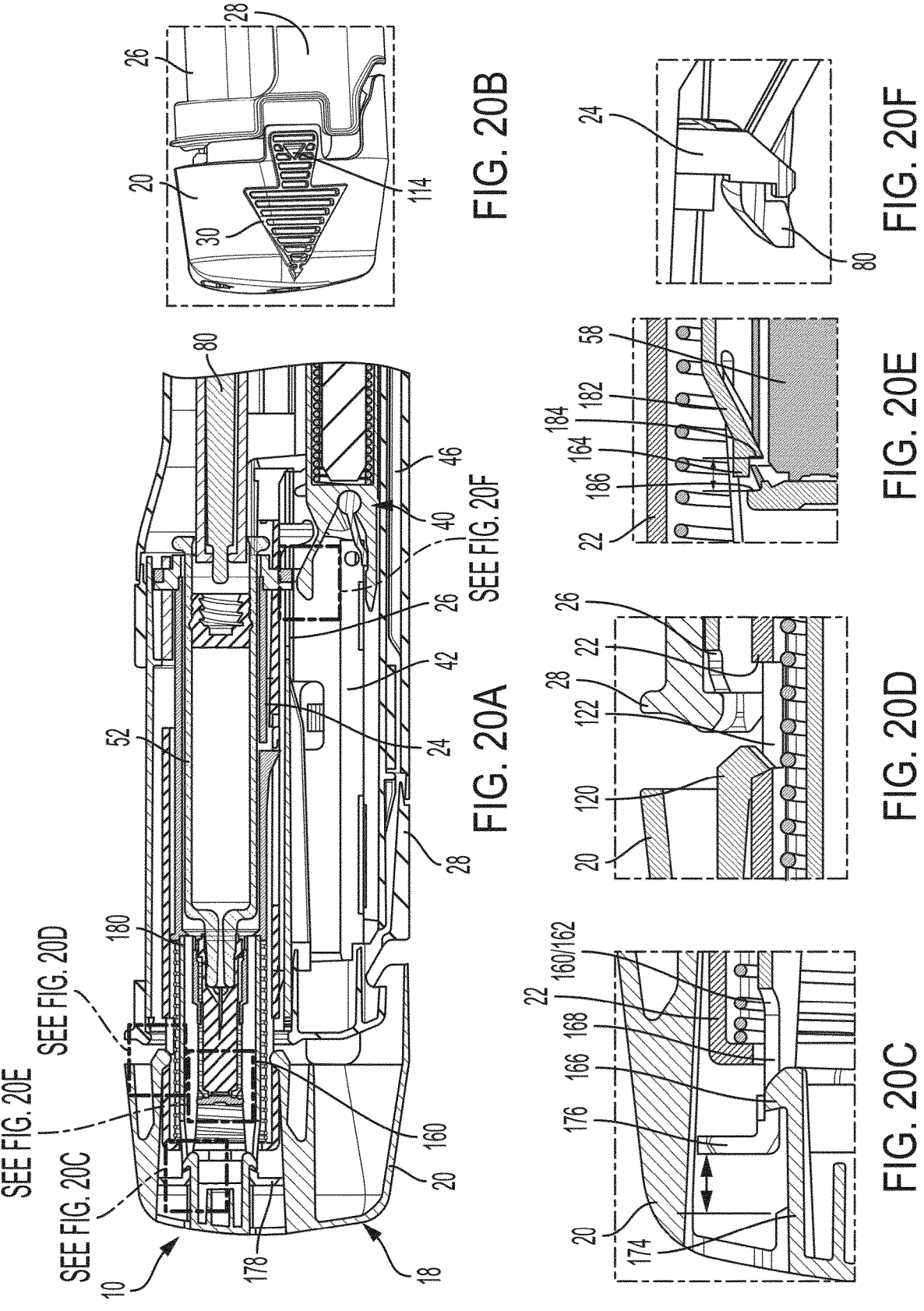
FIG. 20A is a partial cross-sectional view of the drug delivery device of FIG. 1, showing removal of a cap of the device.
FIG. 20B is an enlarged cross-sectional view of the area indicated in FIG. 20A.
FIG. 20C is an enlarged cross-sectional view of the area indicated in FIG. 20A.
FIG. 20D is an enlarged cross-sectional view of the area indicated in FIG. 20A.
FIG. 20E is an enlarged cross-sectional view of the area indicated in FIG. 20A.
FIG. 20F is an enlarged cross-sectional view of the area indicated in FIG. 20A.
Figures 21A, 21B, 21C, 21D, 21E, 21F:
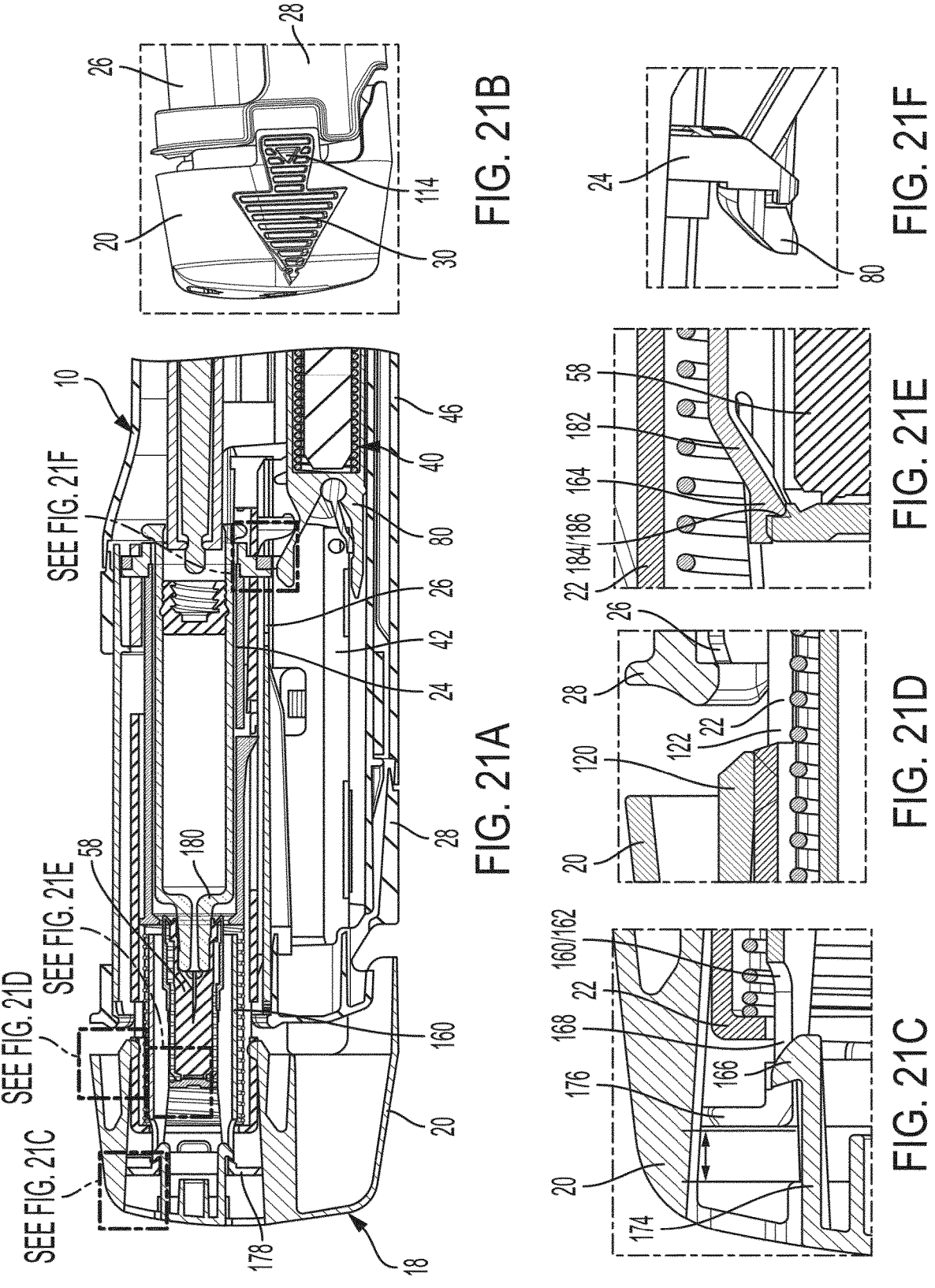
FIG. 21A is a partial cross-sectional view of the drug delivery device of FIG. 1, showing removal of a cap of the device.
FIG. 21B is an enlarged cross-sectional view of the area indicated in FIG. 21A.
FIG. 21C is an enlarged cross-sectional view of the area indicated in FIG. 21A.
FIG. 21D is an enlarged cross-sectional view of the area indicated in FIG. 21A.
FIG. 21E is an enlarged cross-sectional view of the area indicated in FIG. 21A.
FIG. 21F is an enlarged cross-sectional view of the area indicated in FIG. 21A.
Figures 22A, 22B, 22C, 22D, 22E, 22F:
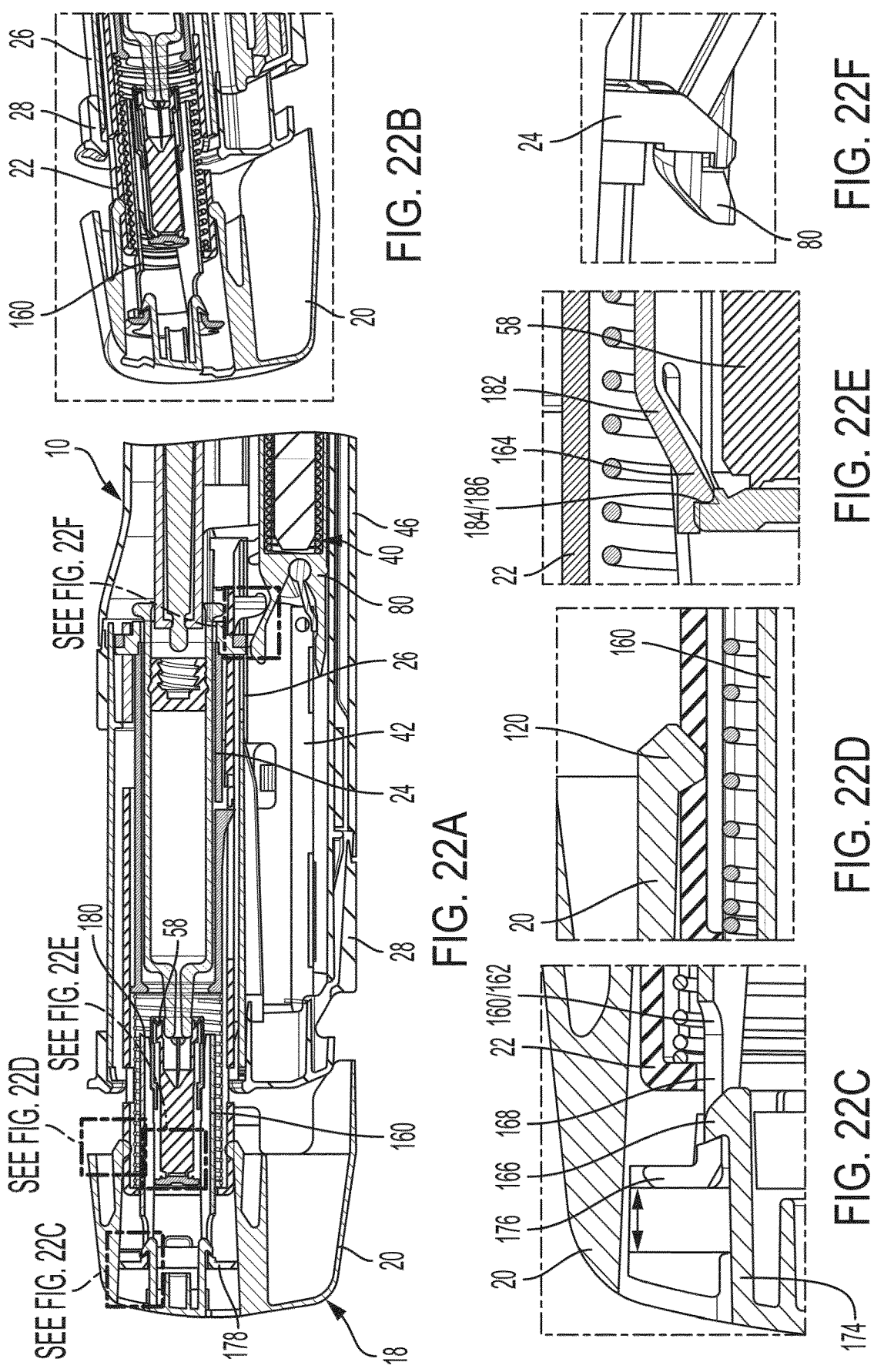
FIG. 22A is a partial cross-sectional view of the drug delivery device of FIG. 1, showing removal of a cap of the device.
FIG. 22B is an enlarged cross-sectional view of the area indicated in FIG. 22A.
FIG. 22C is an enlarged cross-sectional view of the area indicated in FIG. 22A.
FIG. 22D is an enlarged cross-sectional view of the area indicated in FIG. 22A.
FIG. 22E is an enlarged cross-sectional view of the area indicated in FIG. 22A.
FIG. 22F is an enlarged cross-sectional view of the area indicated in FIG. 22A.
Figure 24:
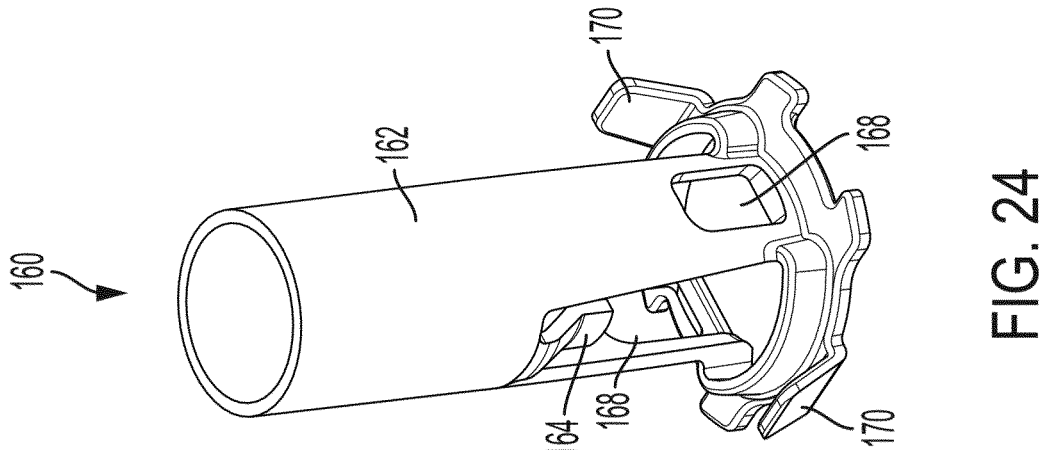
FIG. 24 is a perspective view of a retainer according to one aspect of the present application.

As shown in FIG. 17C, the retaining tab 166 of the outer portion 20 is disengaged from the retainer 160 when the outer portion 20 is secured to the lower housing shell 28 with the device 10 in the storage position. As shown in FIGS. 20C, 21C, and 22C, the retaining tab 166 of the outer portion 20 is disengaged from the retainer 160 when the outer portion 20 is secured to the lower housing shell 28. The retaining tab 166 of the outer portion 20 is secured to the body 116 of the outer portion 20 via an extension arm 174. The retaining tab 166 is moveable radially inward via the extension arm 174. The flexibility of the extension arm 174 facilitates the assembly of the retainer 160 to the outer portion 20 by allowing the retaining tab 166 to deflect radially inward as the retaining tab 166 engages the retainer 160 until the retaining tab 166 is received within the retainer opening 168. The retainer 160 includes a flange 176, which is engaged with the outer portion 20 when the outer portion 20 is secured to the lower housing shell 28. The flange 176 of the retainer 160 is spaced from the outer portion 20 upon axial movement of the outer portion 20 away from the lower housing shell 28.

As shown in FIG. 17E, the body 162 of the retainer 160 is cylindrical and includes a first end 178 and a second end 180 positioned opposite the first end 178. The removal projection 164 extends radially inward from body 162 of the retainer 160 via a removal arm 182. The removal arm 182 extends radially inward and in a direction extending from the second end 180 of the body 162 to the first end 178 the body 162, which allows the retainer 160 to be positioned over the RNS 58 and syringe assembly 16 during assembly of the outer portion 20 and the retainer 160 onto the device 10. The removal projection 164 is moveable relative to the body 162 of the retainer 160 via the removal arm 182. More specifically, the removal projection 164 is moveable radially outward during assembly of the retainer 160 to the RNS 58 and moveable radially inward during removal of the outer portion 20 and the retainer 160. The removal projection 164 includes a surface 184 that is configured to engage a complementary surface 186 of the RNS 58. The surface 184 of the removal projection 164 of the retainer 160 is disengaged from the corresponding surface 186 of the RNS 58 when the outer portion 20 is secured to the lower housing shell 28. The surface 184 of the removal projection 164 is planar, although other suitable shapes and configurations may be utilized. The corresponding surface 186 of the RNS 58 is planar, although other suitable shapes and configurations may be utilized. The corresponding surface 186 of the RNS 58 is defined by a flange portion of the RNS 58.

Figures 19A, 19B, 19C, 19D, 19E, 19F:
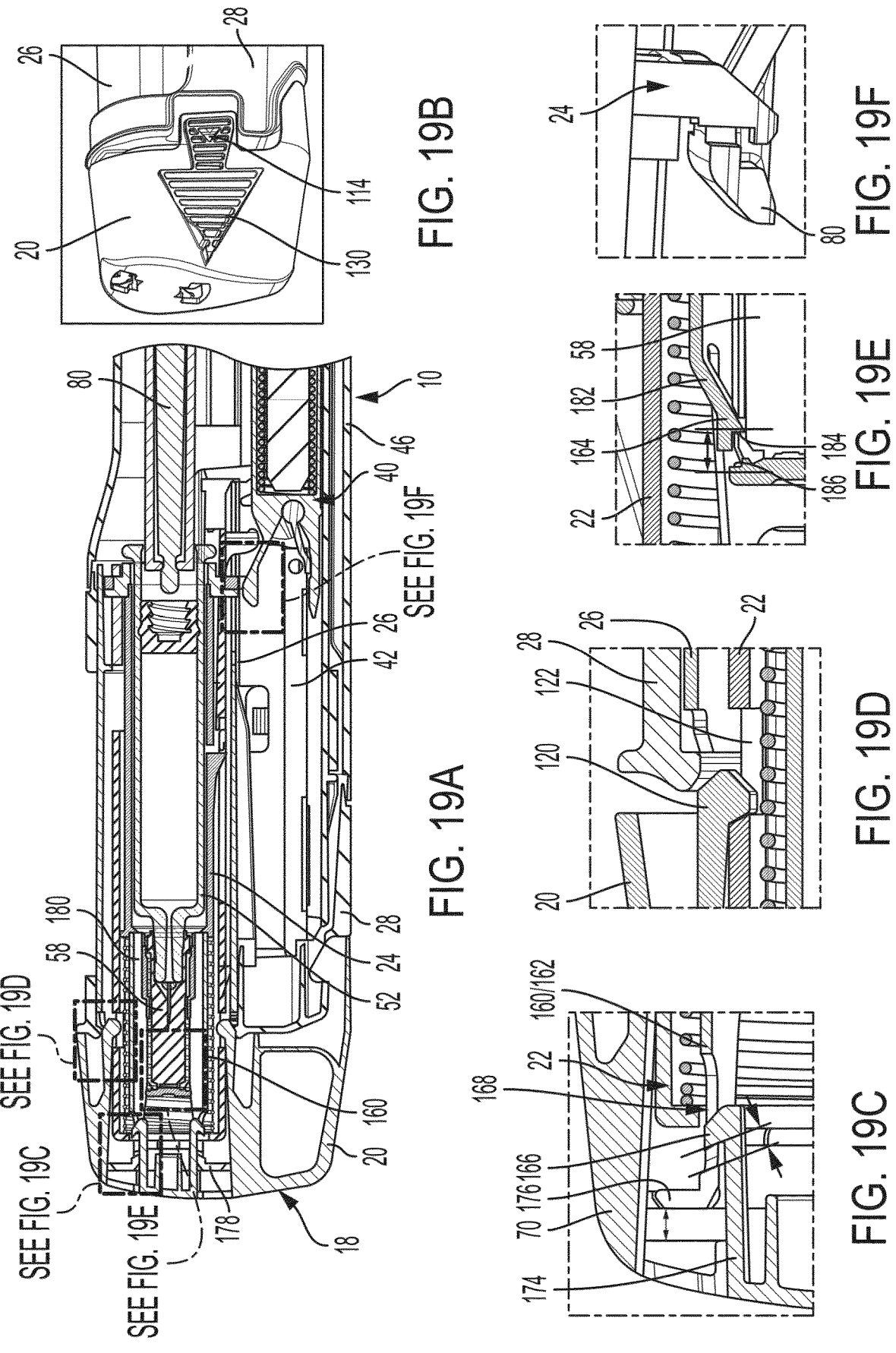
FIG. 19A is a partial cross-sectional view of the drug delivery device of FIG. 1, showing removal of a cap of the device.
FIG. 19B is an enlarged cross-sectional view of the area indicated in FIG. 19A.
FIG. 19C is an enlarged cross-sectional view of the area indicated in FIG. 19A.
FIG. 19D is an enlarged cross-sectional view of the area indicated in FIG. 19A.
FIG. 19E is an enlarged cross-sectional view of the area indicated in FIG. 19A.
FIG. 19F is an enlarged cross-sectional view of the area indicated in FIG. 19A.

Referring to FIG. 17F, the syringe holder 24 is disengaged with the plunger body 80 of the drive assembly 40 when the outer portion 20 is secured to the lower housing shell 28. Referring to FIG. 19F, for example, the syringe holder 24 is engaged with the plunger body 80 of the drive assembly 40 upon axial movement of the outer portion 20 of the cap 18 away from the lower housing shell 28. More specifically, a pair of arms extend from the syringe holder 24 and engage the audio indicator member 94 of the plunger body 80, although other suitable configurations may be utilized. The engagement between syringe holder 24 and the plunger body 80 of the drive assembly 40 prevents the removal of the outer portion 20 and the RNS 58 from moving the syringe holder 24 relative to the cassette body 26 due to the friction between the syringe assembly 16 and the syringe holder 24. The engagement between the syringe holder 24 and the plunger body 80 also restricts the axial movement of the syringe holder 24 within the device 10 caused by movement of the device 10 or by gravity when the device is in the pre-use position.

Referring to FIGS. 17A-17F, when the device 10 is in the storage position with the outer portion 20 secured to the lower shell assembly 28, the flange 176 of the retainer 160 abuts the outer portion 20 (FIG. 17B), the retaining tab 166 of the outer portion 20 is positioned within the retainer opening 168 and spaced from the proximal portion of the body 162 of the retainer 160 (FIG. 17C), the protrusion 120 of the cap is received within the cap opening 122 of the needle cover 22 and spaced from the needle cover 22 (FIG. 17D), the surface 184 of the removal projection 164 is spaced from the corresponding surface 186 of the RNS 58 (FIG. 17E), and the syringe holder 24 is spaced from the plunger body 80 of the drive assembly 40 (FIG. 17F). In the storage position of the device 10, the retainer 160 is engaged with the syringe holder 24. When the flange 176 of the retainer 160 abuts the outer portion 20, the planar surface 184 of the removal projection 164 of the retainer 160 is properly positioned relative to the complementary surface 186 of the RNS 58. In other words, abutment of the flange 176 with the outer portion 20 ensures the retainer 160 is sufficiently positioned axially towards the lower housing shell 28 to allow removal of the RNS 58 as described below.

Figures 18A, 18B, 18C, 18D, 18E, 18F:
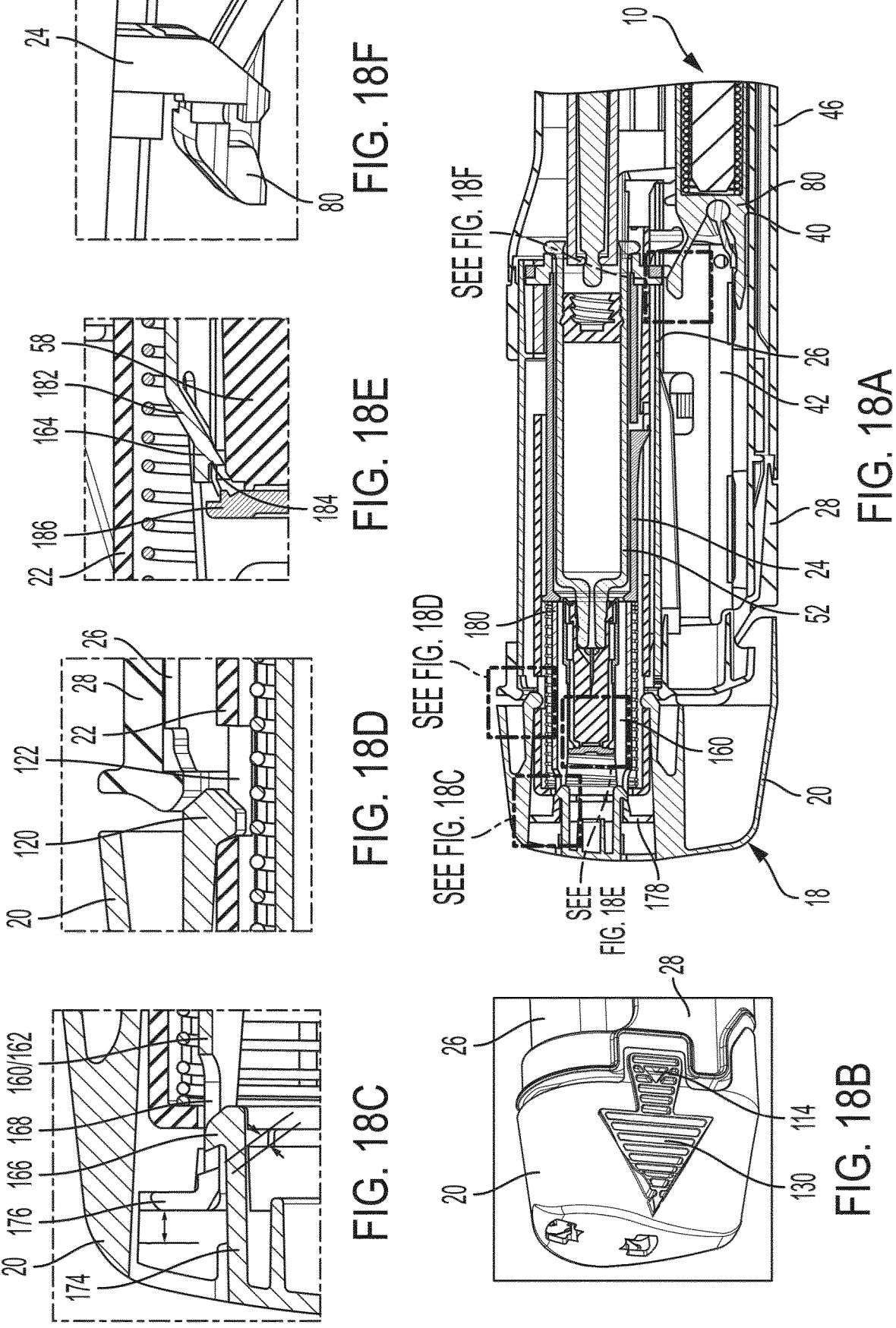
FIG. 18A is a partial cross-sectional view of the drug delivery device of FIG. 1, showing an initial removal of a cap of the device.
FIG. 18B is an enlarged cross-sectional view of the area indicated in FIG. 18A.
FIG. 18C is an enlarged cross-sectional view of the area indicated in FIG. 18A.
FIG. 18D is an enlarged cross-sectional view of the area indicated in FIG. 18A.
FIG. 18E is an enlarged cross-sectional view of the area indicated in FIG. 18A.
FIG. 18F is an enlarged cross-sectional view of the area indicated in FIG. 18A.

Referring to FIGS. 18A-18F, as the outer portion 20 is initial axially moved away from the lower housing shell 28 (FIG. 18B) with the lock protrusion 112 only partially received within the lock recess 114, the flange 176 of the retainer 160 is spaced from the outer portion 20 and the retaining tab 166 is still spaced from the body 162 of the retainer 160 (FIG. 18C), the protrusion 120 of the outer portion 20 is engaged with the needle cover 22 (FIG. 18D), the surface 184 of the removal projection 164 is spaced from the corresponding surface 186 of the RNS 58 (FIG. 18E), and the syringe holder 24 is spaced from the plunger body 80 of the drive assembly 40 (FIG. 18F).

Referring to FIGS. 19A-19F, as the outer portion 20 continues to be axially moved away from the lower housing shell 28 (FIG. 19B) with the lock protrusion 112 only partially received within the lock recess 114, the flange 176 of the retainer 160 is spaced from the outer portion 20 and the retaining tab 166 is still spaced from the body 162 of the retainer 160 (FIG. 19C), the protrusion 120 of the outer portion 20 is engaged with the needle cover 22 (FIG. 19D), the surface 184 of the removal projection 164 is spaced from the corresponding surface 186 of the RNS 58 (FIG. 19E), and the syringe holder 24 is engaged with the plunger body 80 of the drive assembly 40 (FIG. 19F).

Referring to FIGS. 20A-20F, as the outer portion 20 continues to be axially moved away from the lower housing shell 28 (FIG. 20B) with the lock protrusion 112 separated from the lock recess 114, the flange 176 of the retainer 160 is further spaced from the outer portion 20 and the retaining tab 166 is engaged with the body 162 of the retainer 160 (FIG. 20C) such that the outer portion 20 and the retainer 160 move together axially away from the lower housing shell 28, the protrusion 120 of the outer portion 20 disengages with the needle cover 22 (FIG. 20D) and is removed from the cap opening 122, the surface 184 of the removal projection 164 is spaced from the corresponding surface 186 of the RNS 58 (FIG. 20E), and the syringe holder 24 is engaged with the plunger body 80 of the drive assembly 40 (FIG. 20F).

Referring to FIGS. 21A-21F, as the outer portion 20 continues to be axially moved away from the lower housing shell 28 (FIG. 21B), the flange 176 of the retainer 160 is spaced from the outer portion 20 and the retaining tab 166 is engaged with the body 162 of the retainer 160 (FIG. 21C) such that the outer portion 20 and the retainer 160 move together axially away from the lower housing shell 28, the protrusion 120 of the outer portion 20 continues to be disengaged from the needle cover 22 (FIG. 21D), the surface 184 of the removal projection 164 engages the corresponding surface 186 of the RNS 58 (FIG. 21E), and the syringe holder 24 is engaged with the plunger body 80 of the drive assembly 40 (FIG. 21F).

Referring to FIGS. 22A-22F, as the outer portion 20 continues to be axially moved away from and separated from the lower housing shell 28 (FIG. 22B), the flange 176 of the retainer 160 is spaced from the outer portion 20 and the retaining tab 166 is engaged with the body 162 of the retainer 160 (FIG. 22C) such that the outer portion 20 and the retainer 160 move together axially away from the lower housing shell 28, the protrusion 120 of the outer portion 20 continues to be disengaged from the needle cover 22 (FIG. 22D), the surface 184 of the removal projection 164 continues to be engaged with the corresponding surface 186 of the RNS 58 and axially displaces the RNS 58 relative to the barrel 52 of the syringe assembly 16 (FIG. 22E), and the syringe holder 24 is engaged with the plunger body 80 of the drive assembly 40 (FIG. 22F).

Figure 23:
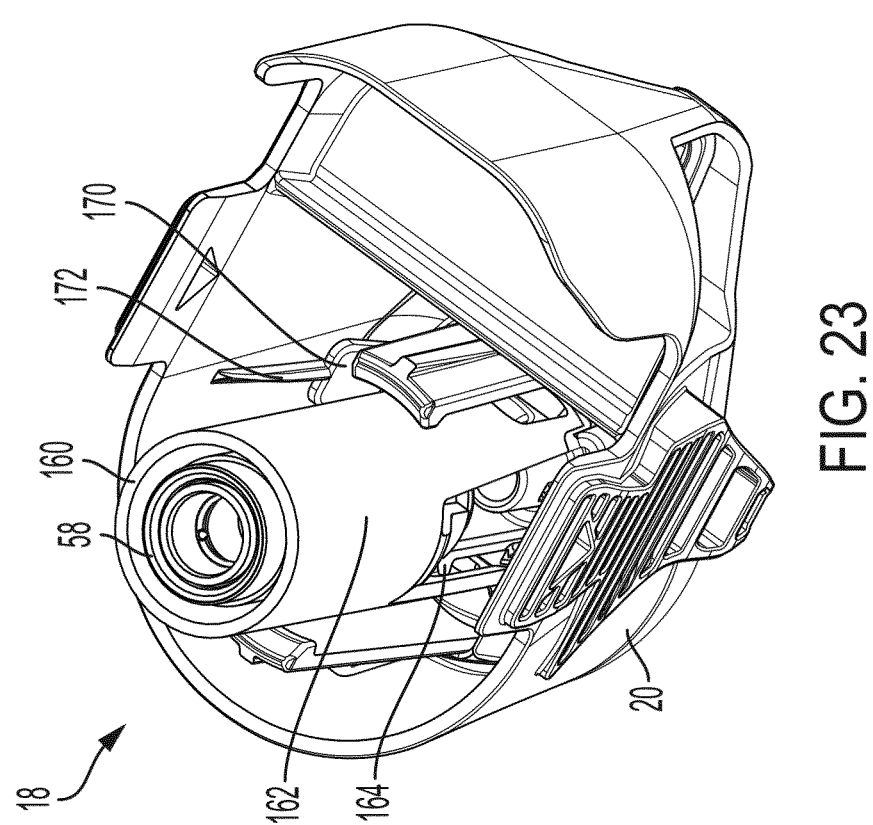
FIG. 23 is a perspective view of a cap, retainer, and rigid needle shield according to one aspect of the present application.
Figure 25:
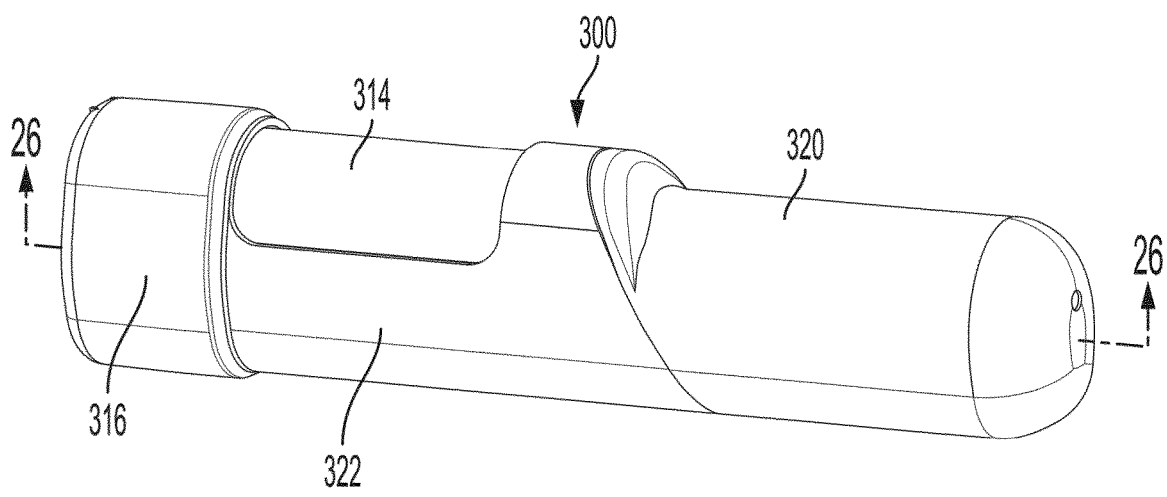
FIG. 25 is a perspective view of a drug delivery device according to a further aspect of the present application, showing a storage position of the device.
Figure 26:
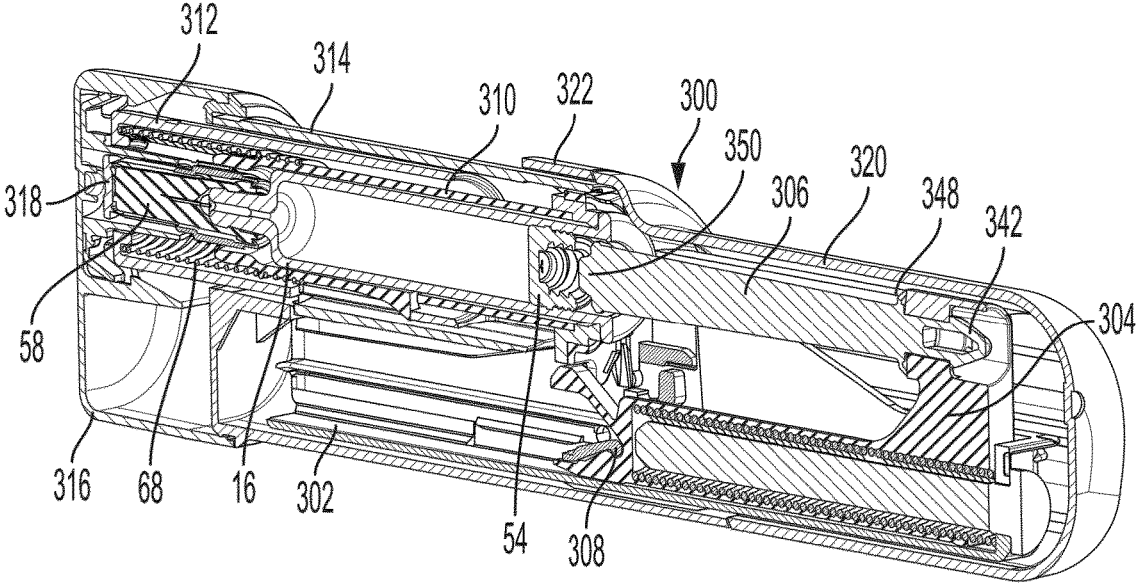
FIG. 26 is a cross-sectional view taken along line 26-26 shown in FIG. 25.
Figure 27:
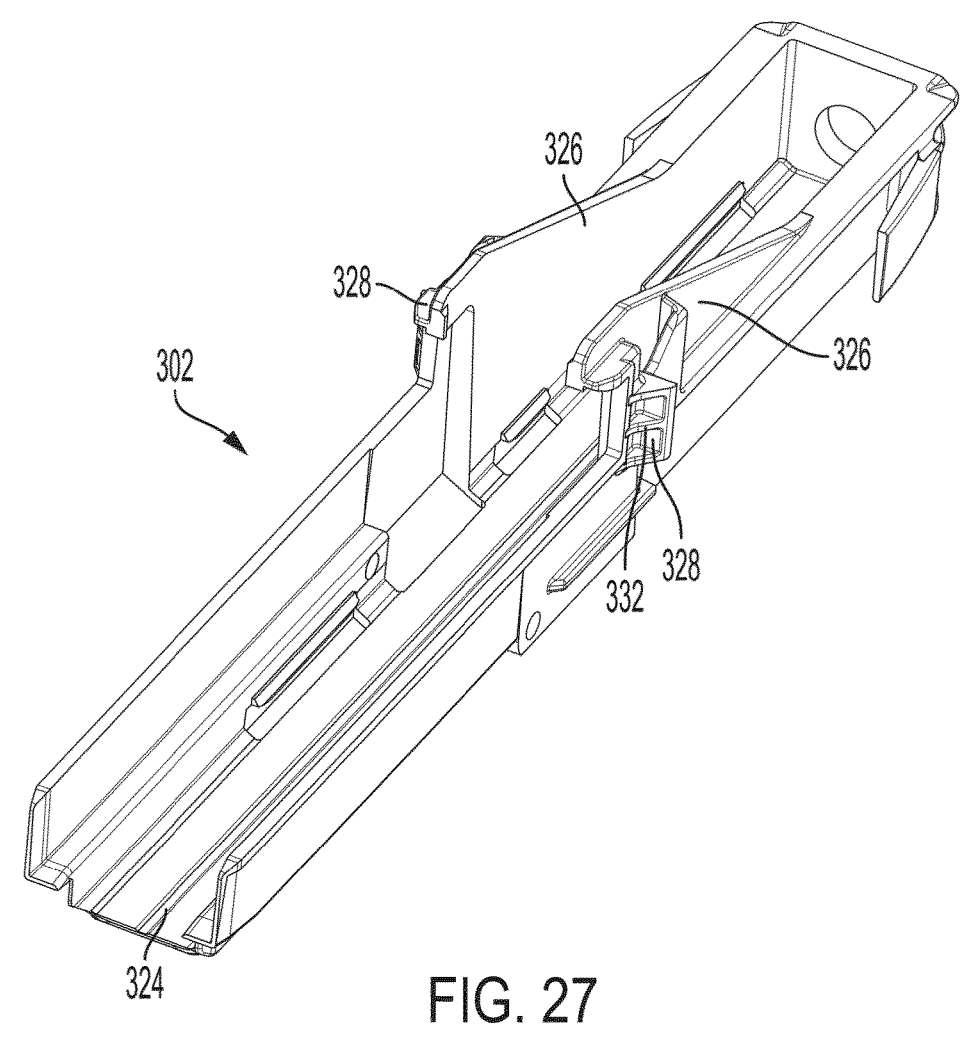
FIG. 27 is a top perspective view of a motor body of the drug delivery device of FIG. 25.
Figure 28:
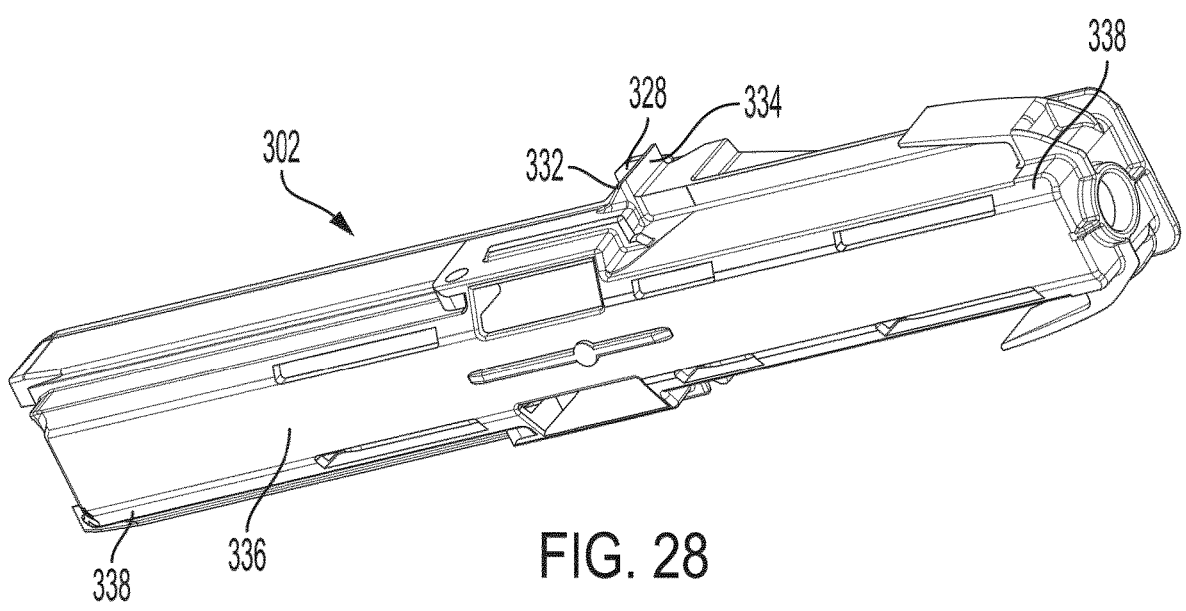
FIG. 28 is a bottom perspective view of the motor body of FIG. 27.
Figures 29, 30:
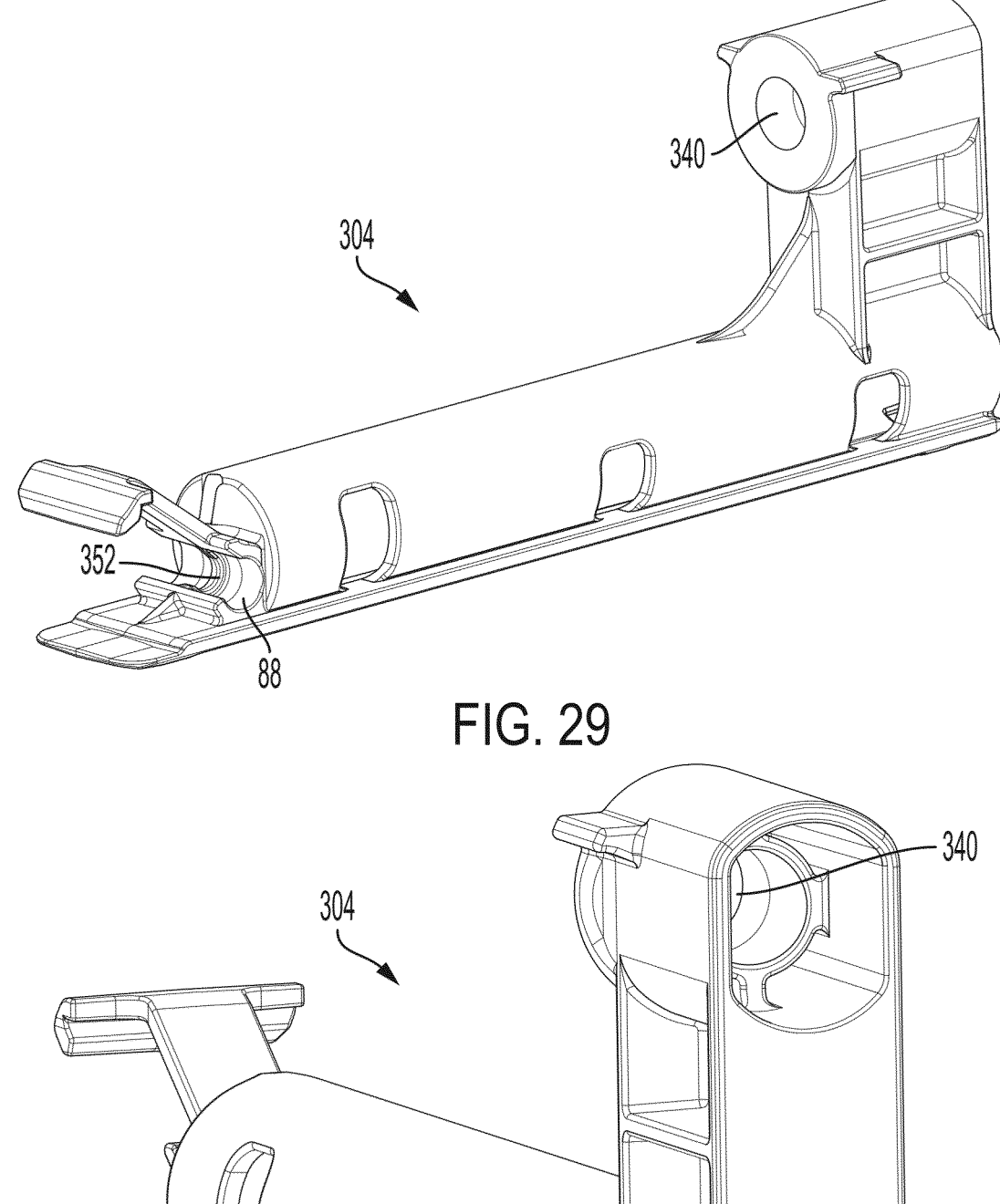
FIG. 29 is a front perspective view of a plunger body of the drug delivery device of FIG. 25.
FIG. 30 is a rear perspective view of the plunger body of FIG. 29.
Figure 31:
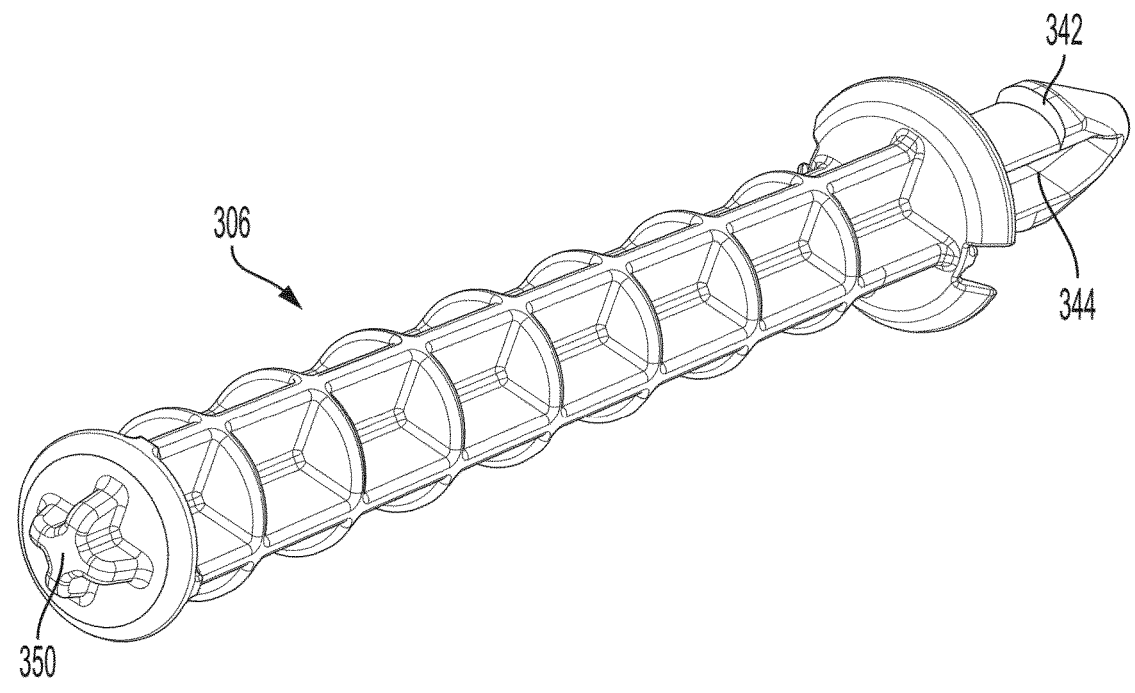
FIG. 31 is a front perspective view of a plunger rod portion of the drug delivery device of FIG. 25.
Figure 32:
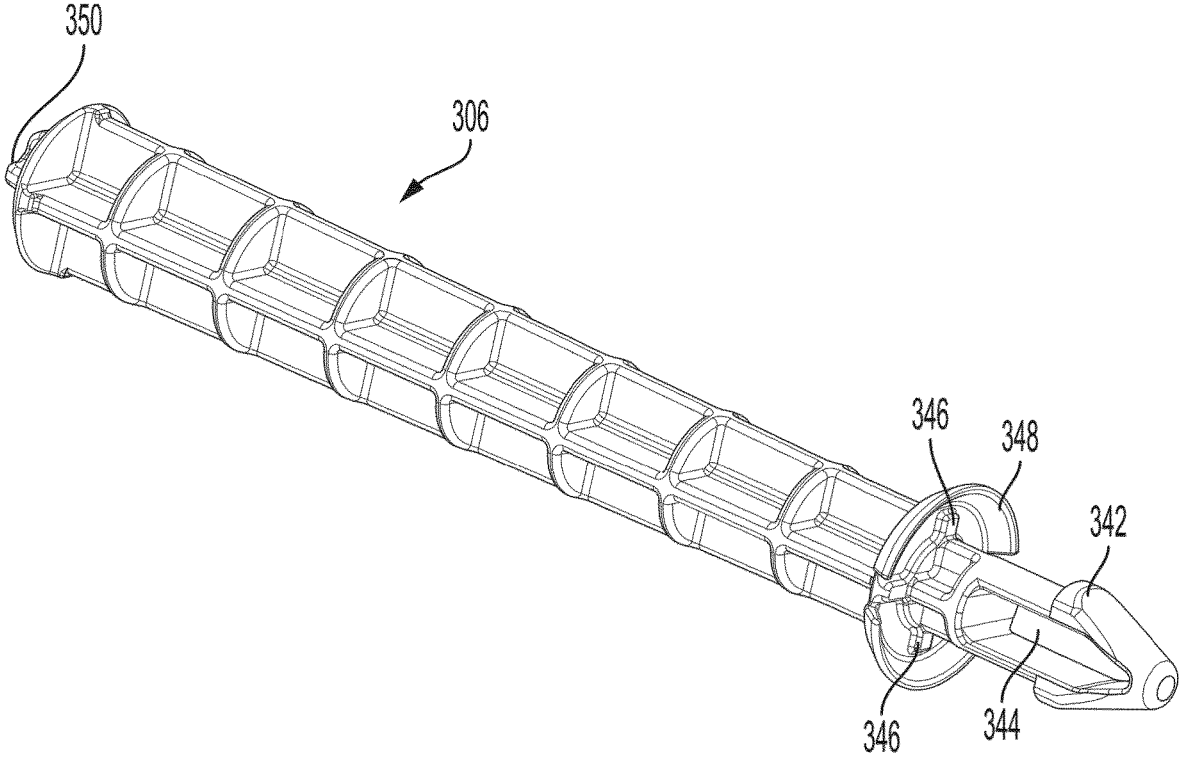
FIG. 32 is a rear perspective view of the plunger rod portion of FIG. 31.

Referring to FIG. 23, upon complete removal of the outer portion 20 from the lower housing shell 28, the RNS 58 continues to remain engaged with the retainer 160 with the RNS 58 entirely separated from the barrel 552 of the syringe assembly 16.

Referring again to FIGS. 17A-24, as discussed above, the outer portion 20 and the retainer 160 are configured to minimize the amount of force required to remove the outer portion 20 and retainer 160 from the device 10 by separating the various components from each other sequentially, rather than at the same time. By sequencing the removal of the outer portion 20 from the lower housing shell 28, the separation of the protrusion 120 of the outer portion 20 from the needle cover 22, and the removal of the RNS 58 from the syringe assembly 16, a patient is only required to apply sufficient force for each step in the sequence rather than a larger force that would be required to remove such components at the same time. As discussed above, such sequencing is provided via the relative movement between the outer portion 20 and the retainer 160, relative movement between the outer portion 20 and the needle cover 22, and the relative movement between the retainer 160 and the RNS 58.

Referring to FIGS. 25-49, a drug delivery device 300 according to a further aspect of the present invention is shown. The drug delivery device 300 is similar to the drug delivery device 10 shown in FIGS. 1A-24, with certain differences discussed below in detail. The drug delivery device 300 includes, among other components, a motor body 302, a plunger body 304, a plunger rod portion 306, a lever actuation member 308, a syringe holder 310, a needle cover 312, a cassette body 314, a cap 316, a retainer 318, an upper housing shell 320, and a lower housing shell 322.

Referring to FIGS. 24-28, the motor body 302 is similar and functions similarly to the motor body 42 of FIGS. 1A-24, but further includes a longitudinal groove 324, reinforcing rib(s) 326, and cassette clip(s) 328. The longitudinal groove 324 is configured to receive a molding split line of the plunger body 304 to ensure smooth sliding between the motor body 302 and the plunger body 304. The reinforcing rib(s) 326 provide additional support for the pair of arms 260 of the motor body 302. The cassette clip(s) 328 is received by an opening(s) 330 defined by the cassette body 314 to secure the motor body 302 to the cassette body 314, which is discussed in more detail below. The cassette clip(s) 328 include an angled face 332 and a planar face 334, which is configured to allow insertion of the cassette clip(s) 328 into the opening(s) 330 of the cassette body 314, but prevent the easy removal of the cassette clip(s) 328 once inserted into the opening(s) 330 of the cassette body 314. A bottom surface 336 of the motor body 302 includes chamfered portions 338 to aid assembly of the device 300.

Referring to FIGS. 26 and 29-32, the plunger body 304 is formed separately from the plunger rod portion 306 rather than being formed integrally. Further, the device 300 does not include the plunger rod cover 92. The plunger body 304 defines an opening 340 that receives a plunger rod clip 342 of the plunger rod portion 306. The plunger rod clip 342 is barb-shaped and configured to be inserted into the opening 340 of the plunger body 304, but not easily removed from the opening 340, although other suitable shapes and configurations may be utilized. The plunger rod clip 342 defines a central opening 344, which allows the plunger rod clip 342 to compress as the plunger rod clip 342 is inserted into the opening 340 of the plunger body 304 and expand to its original shape once received within the plunger body 304. The plunger rod portion 306 includes a plunger body stop(s) 346 and a biasing member 348. The plunger body stop(s) 346, which may be one or more projections, contact the plunger body 304 when the plunger rod clip 342 is inserted into the opening 340 of the plunger body 304. The biasing member 348 engages the plunger body 304 during insertion of the plunger rod clip 342 into the opening 340 of the plunger body 304 and biases the plunger rod portion 306 toward the plunger body 304. The biasing member 348 provides additional leeway for insertion of the plunger rod clip 342 into the opening 340 of the plunger body 304 while ensuring there is no gap between the plunger body 304 and the plunger rod portion 306 after assembly. The biasing member 348 of the plunger rod portion 306 is annular, although other suitable shapes and configurations may be utilized.

The plunger rod portion 306 further includes a stopper interface 350 that is received by the stopper 54. The stopper interface 350 is a cruciform projection, although other suitable shapes and configurations may be utilized. The plunger rod portion 306 has a conical external shape configured to reduce stress on the syringe assembly 16, although other suitable shapes may be utilized. The plunger body 304 includes a lever rib 352 extending into the lever opening 88 of the plunger body 304. The lever rib 352 is configured to be received by the lever actuation member 308, as discussed in more detail below.

Figure 33:
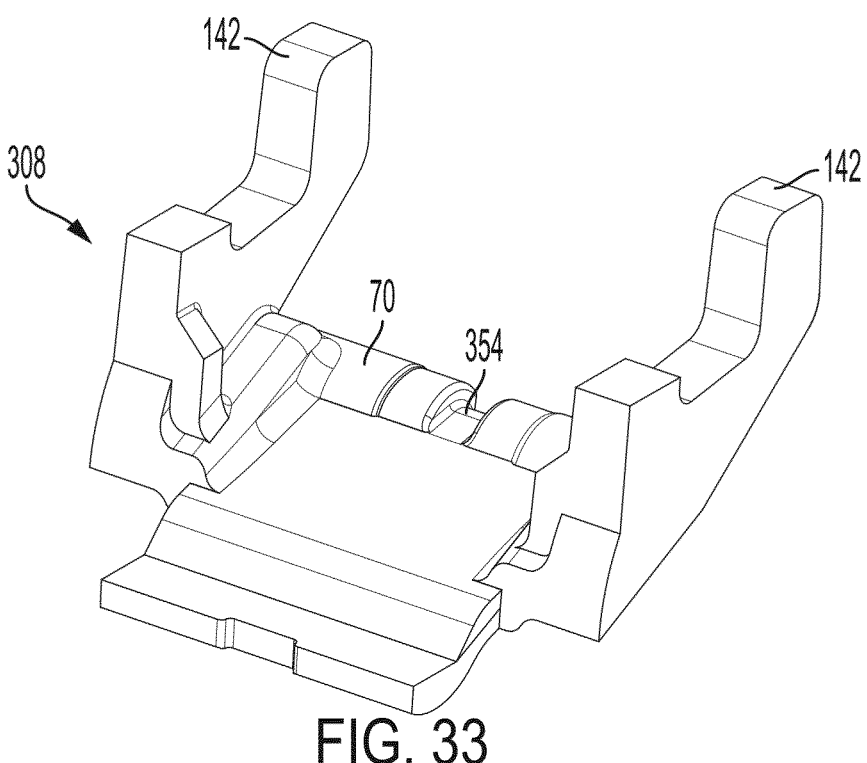
FIG. 33 is a top perspective view of a lever actuation member of the drug delivery device of FIG. 25.
Figure 34:
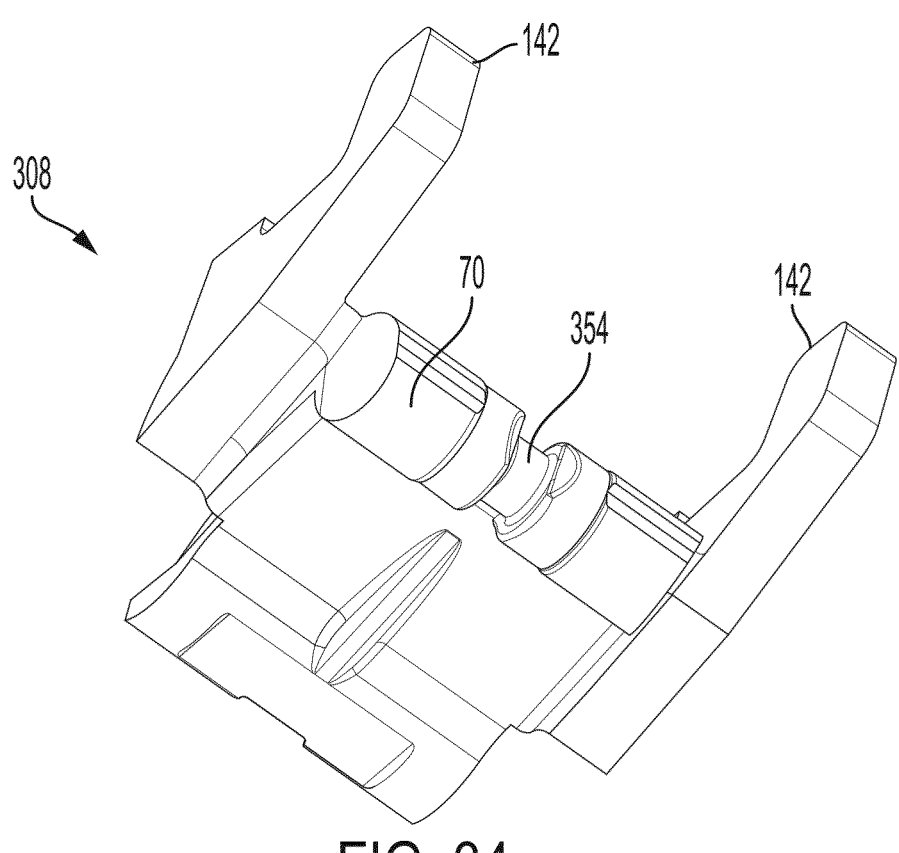
FIG. 34 is a bottom perspective view of the lever actuation member of the drug delivery device of FIG. 33.

Referring to FIGS. 33 and 34, the lever actuation member 308 is similar to and functions similarly to the lever actuation member 44 described above and shown in FIGS. 1A-24. The lever actuation member 308, however, defines a groove 354 at the rotation axis 70 that receives the lever rib 352 of the plunger body 304. The engagement between the groove 354 and the lever rib 352 prevents relative lateral movement between the plunger body 304 and the lever actuation member 308. The needle cover contact surface 142 of the lever actuation member 308 includes a larger surface compared to the needle cover contact surface 142 of the lever actuation member 44 of FIGS. 1A-24.

Figure 35:
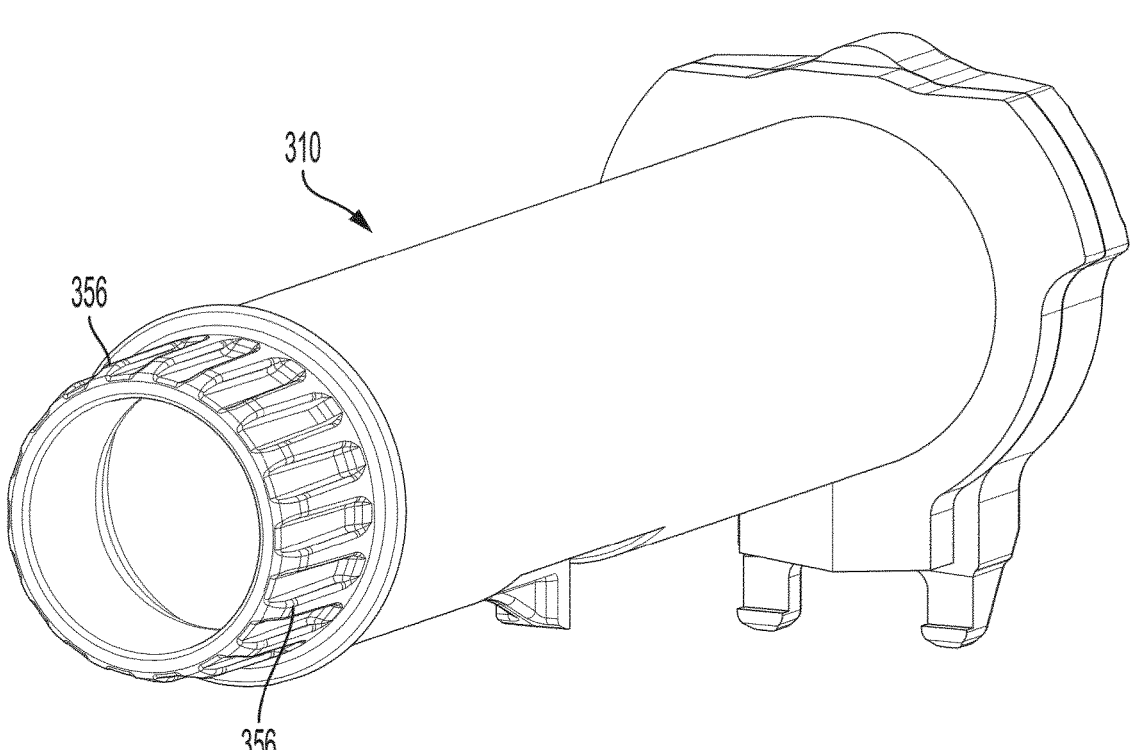
FIG. 35 is a front perspective view of a syringe holder of the drug delivery device of FIG. 25.
Figure 36:
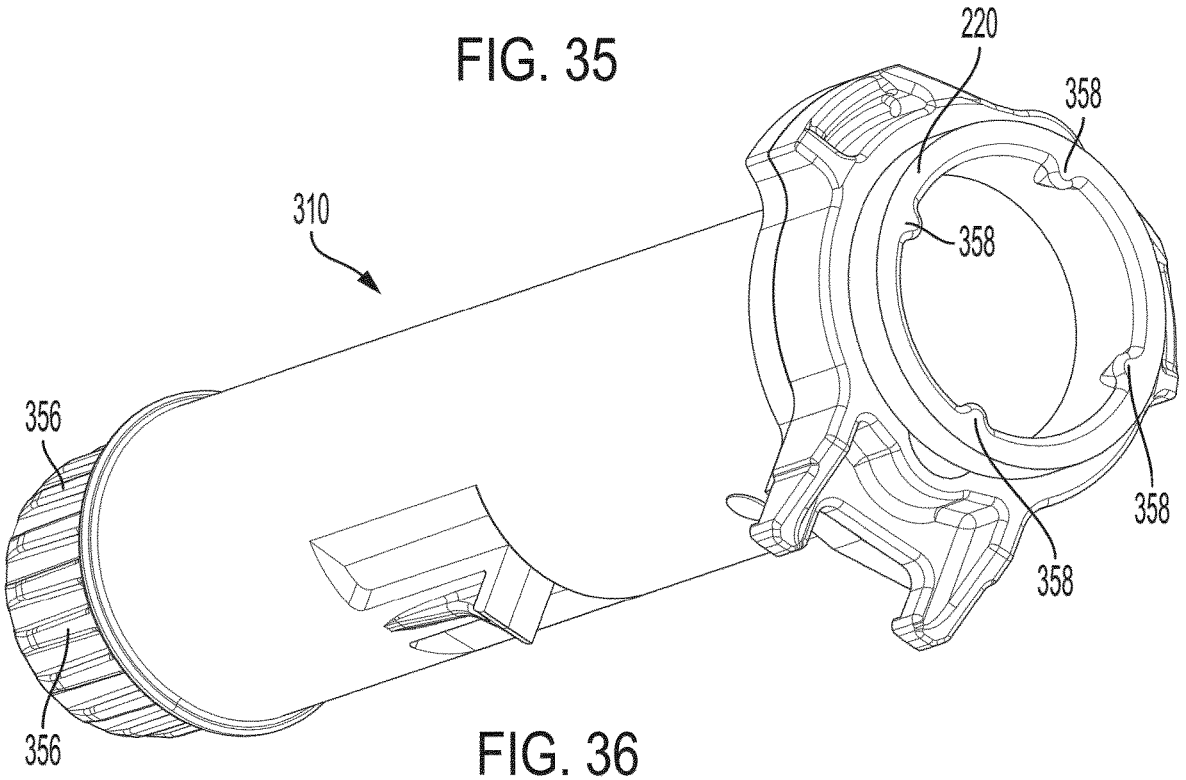
FIG. 36 is a rear perspective view of the syringe holder of the drug delivery device of FIG. 35.

Referring to FIGS. 35 and 36, the syringe holder 310 is similar to and functions similarly to the syringe holder 24 of FIGS. 1A-24. The syringe holder 310, however, further includes a plurality of ribs 356 extending circumferentially around the syringe holder 310. The plurality of ribs engage the spring 68. The securing ring 220 of the syringe holder 310 further includes a plurality of projections 358 that extend radially inward. The plurality of projections 358 engage the syringe assembly 16 to remove any gap between the outer surface of the syringe assembly 16 and the syringe holder 310. The plurality of projections 358 are elastomeric and may compress when the syringe assembly 16 is received within the syringe holder 310.

Figure 37:
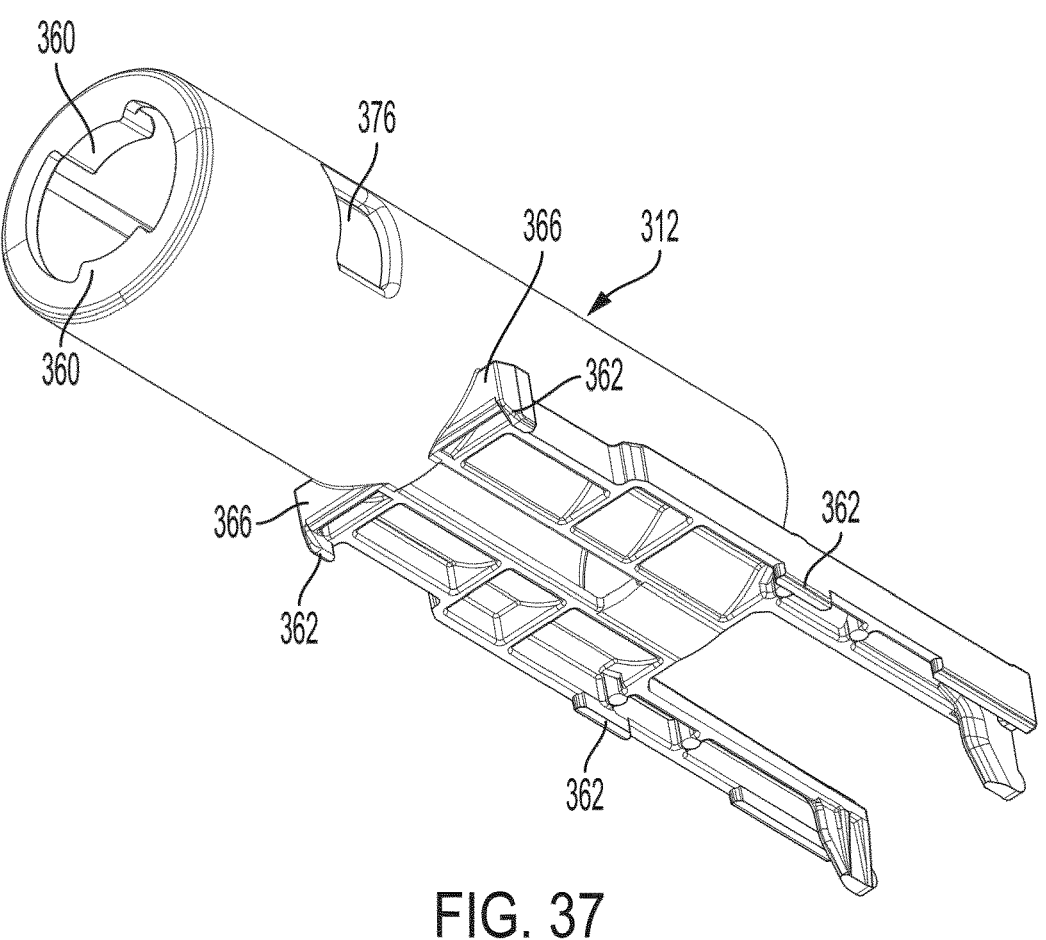
FIG. 37 is a front perspective view of a needle cover of the drug delivery device of FIG. 25.
Figure 38:
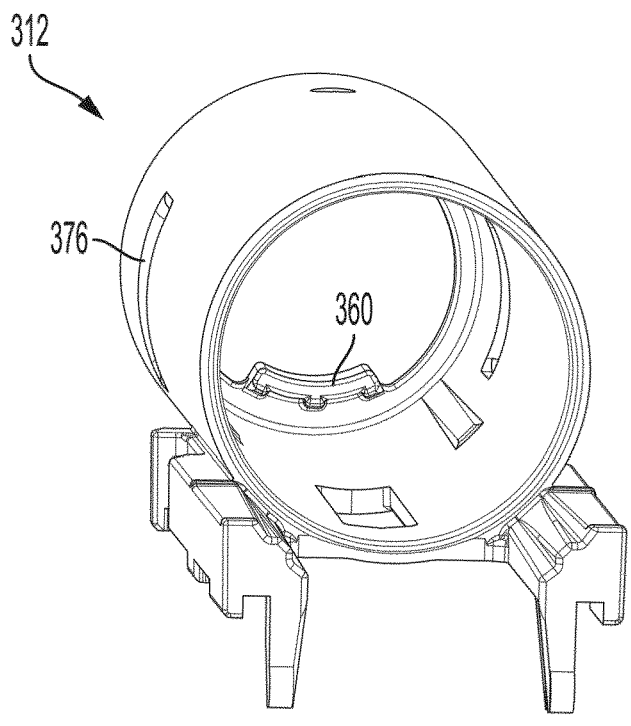
FIG. 38 is a rear perspective view of the needle cover of the drug delivery device of FIG. 37.
Figures 39, 40:
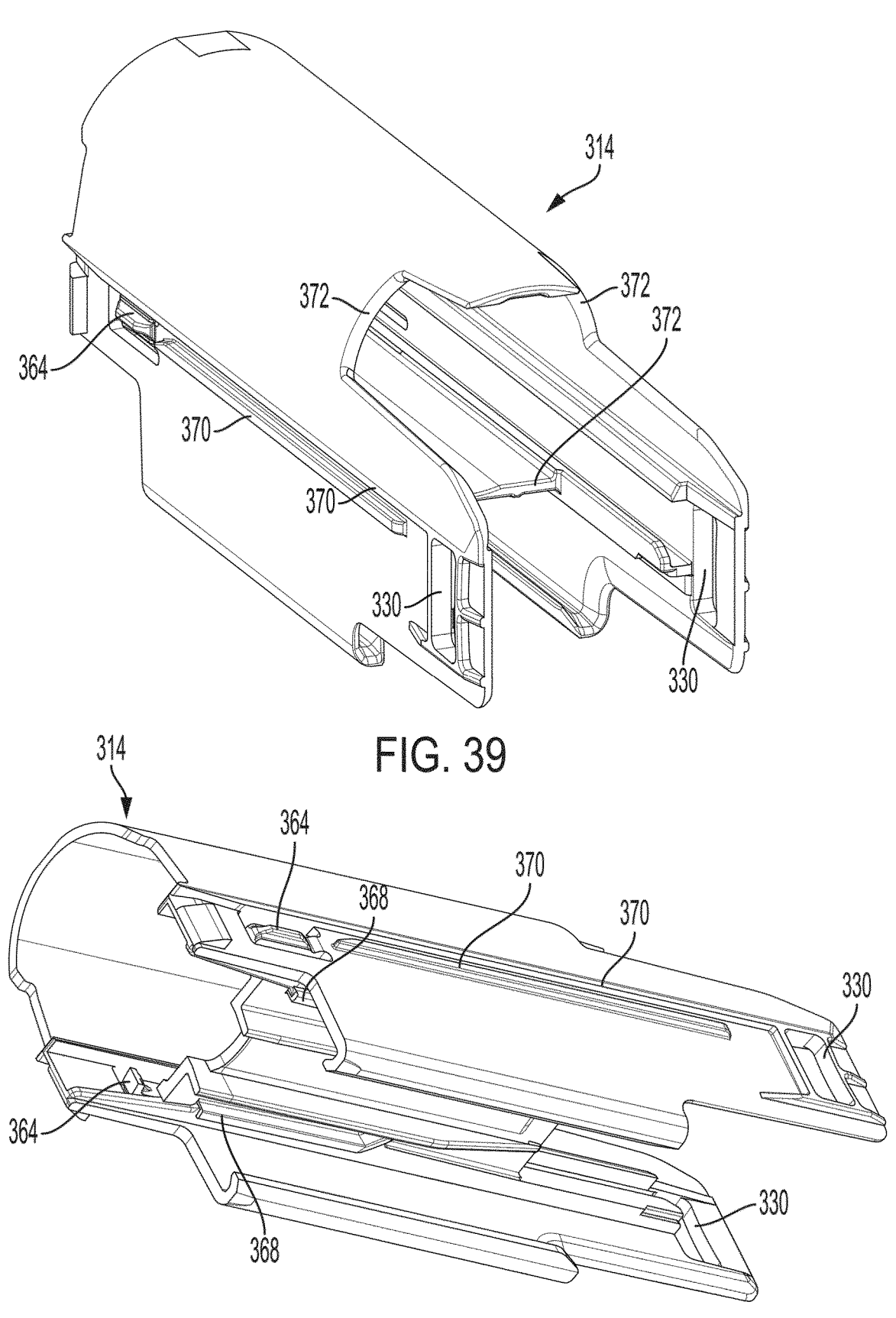
FIG. 39 is a top perspective view of a cassette body of the drug delivery device of FIG. 25.
FIG. 40 is a bottom perspective of the cassette body of the drug delivery device of FIG. 39.
Figure 41:
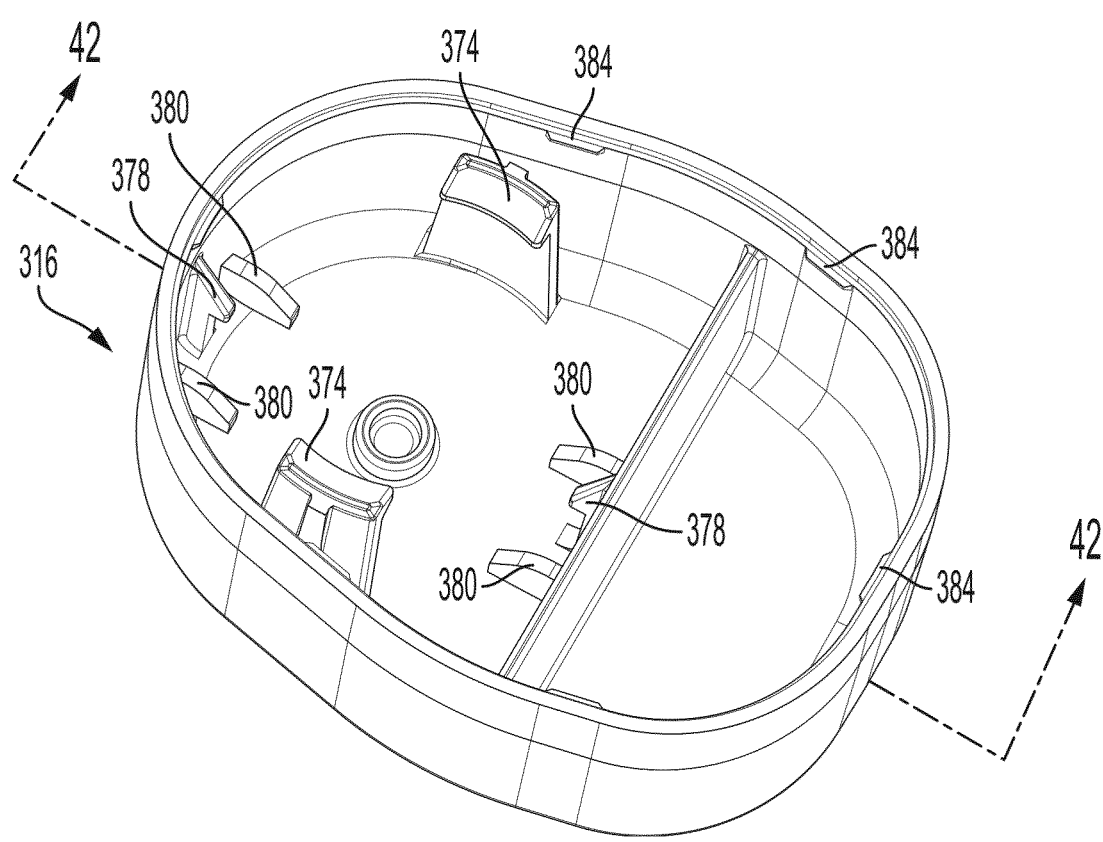
FIG. 41 is a top perspective view of a cap of the drug delivery device of FIG. 25.
Figure 42:
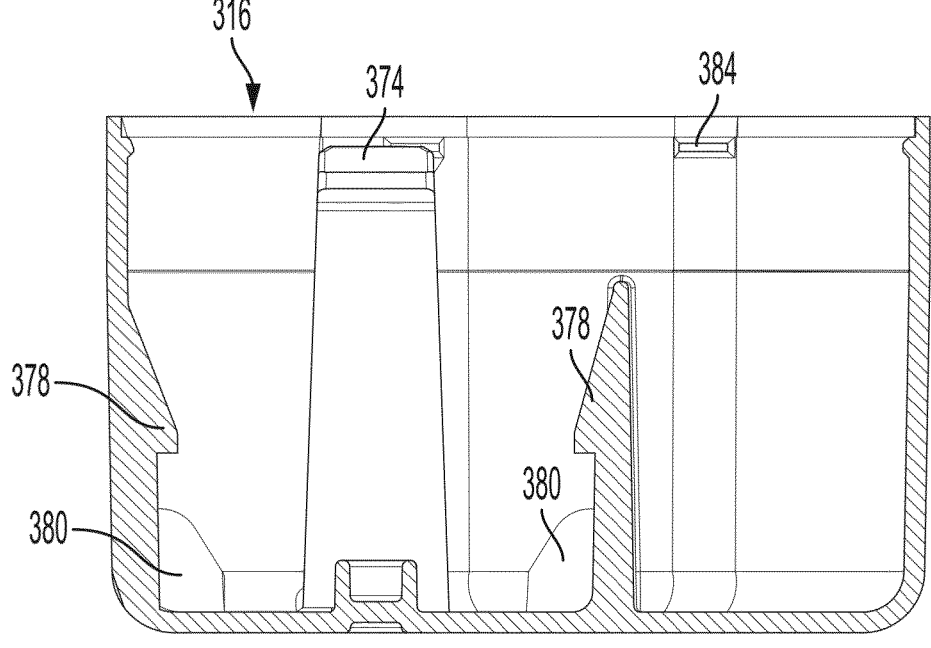
FIG. 42 is a cross-sectional view taken along line 42-42 in FIG. 41.
Figure 43:
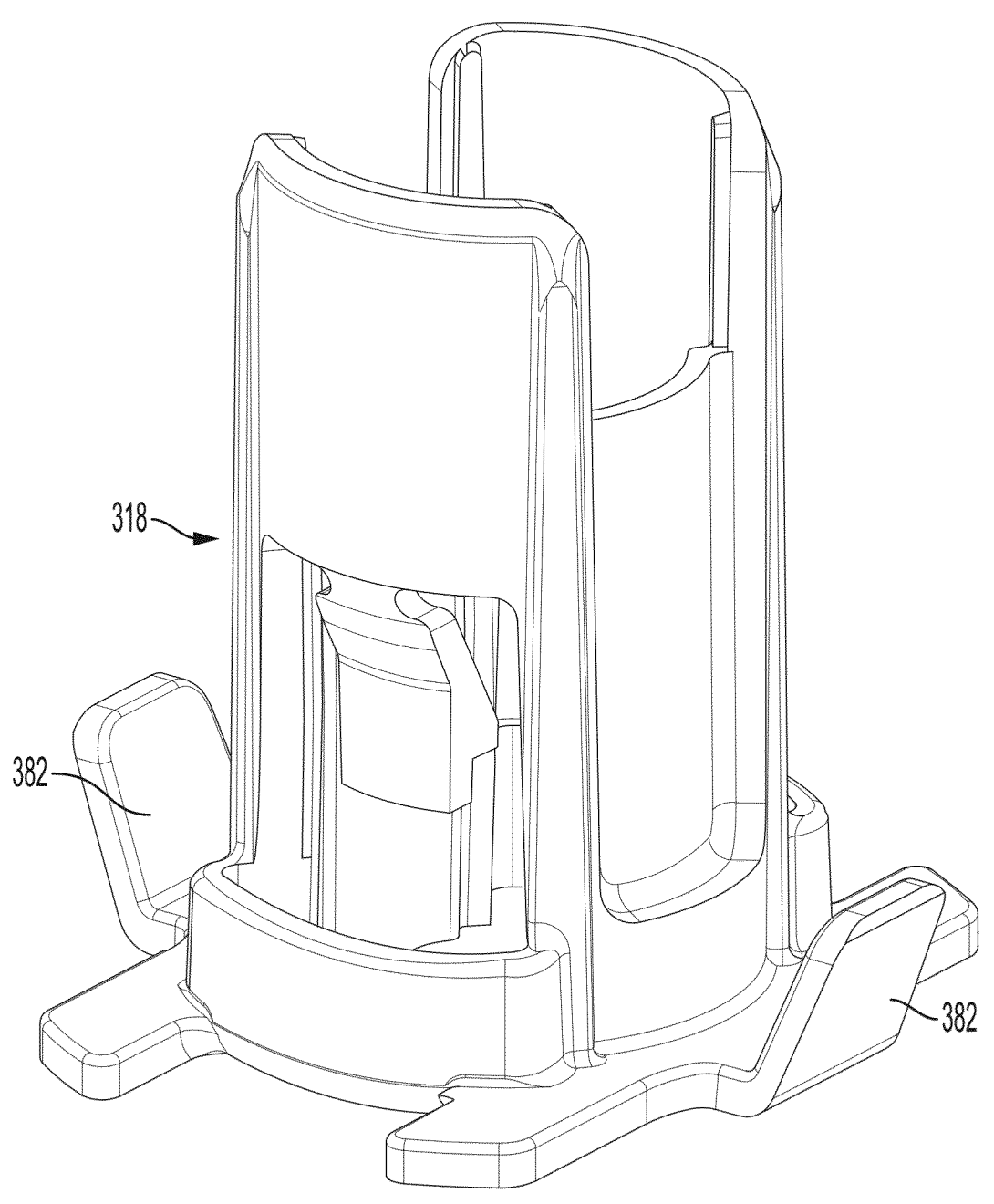
FIG. 43 is a perspective view of a retainer of the drug delivery device of FIG. 25.
Figure 44:
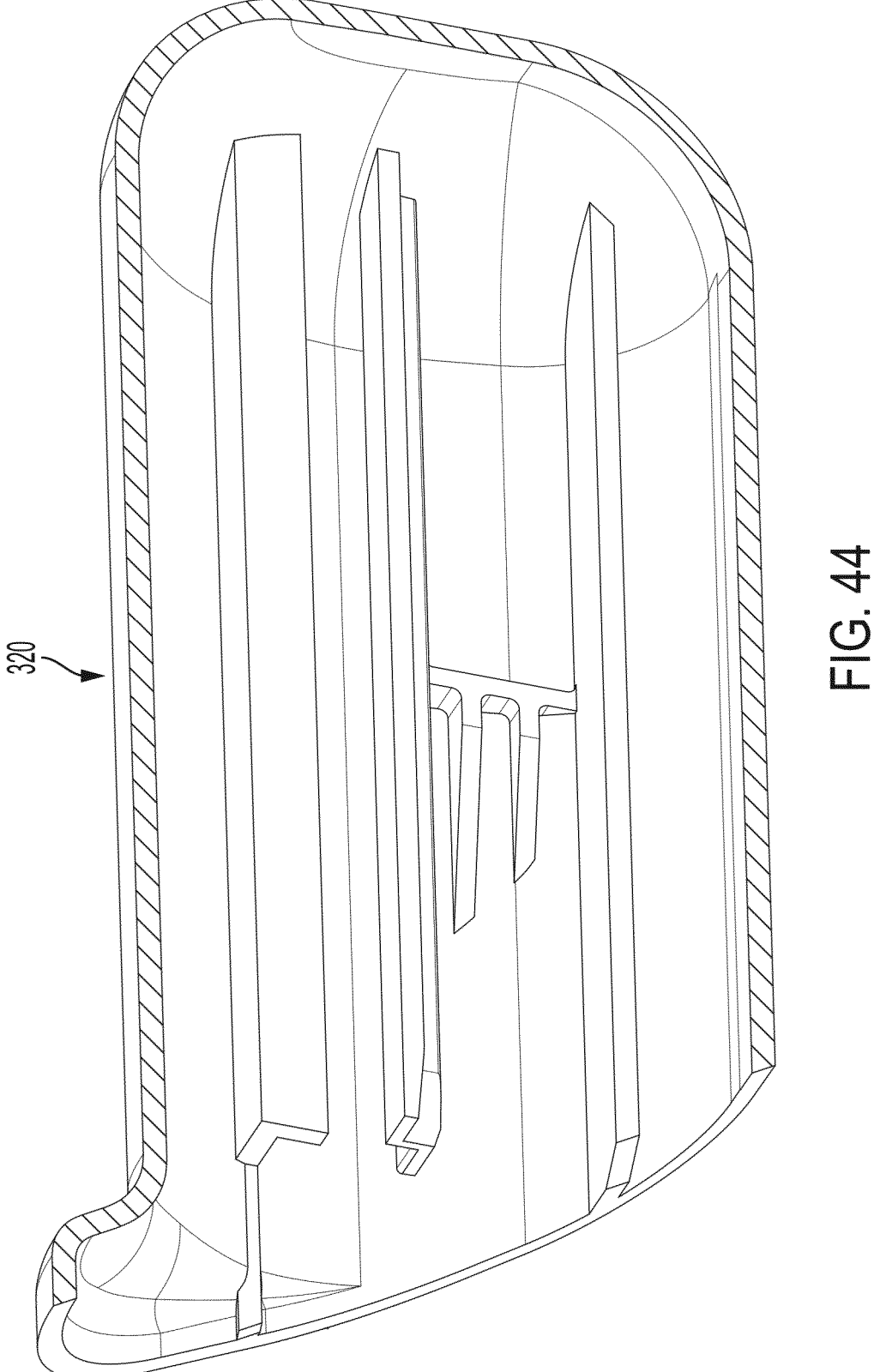
FIG. 44 is a cross-sectional view of an upper housing shell of the drug delivery device of FIG. 25.
Figures 45, 46:
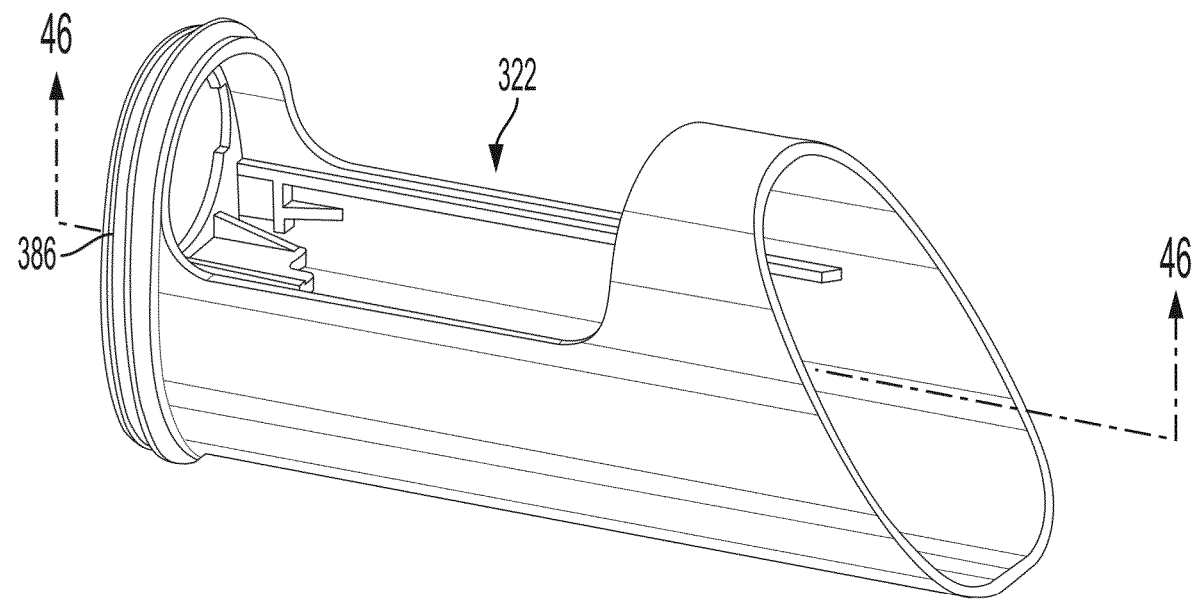
FIG. 45 is perspective view of a lower housing shell of the drug delivery device of FIG. 25.
FIG. 46 is a cross-sectional view taken along line 46-46 in FIG. 45.

Referring to FIGS. 37 and 38, the needle cover 312 is similar to and functions similarly to the needle cover 22 of FIGS. 1A-24. The needle cover 312 includes a spring rib 360 which engages the spring 68 to hold the spring 68 between the needle cover 312 and the syringe holder 310. The needle cover 312 also includes a cassette rib(s) 362 to guide movement of the needle cover 312 relative to the cassette body 314.

Referring to FIGS. 39, 40, 48, and 49, the cassette body 314 is similar to and functions similarly to the cassette body 26 of FIGS. 1A-24. As discussed above, the cassette body 314 includes the opening(s) 330 that receive the cassette clip(s) 328 of the motor body 302. The cassette body 314 includes a needle cover clip(s) 364 that engage clip surface(s) 366 of the needle cover 312. The clip surface(s) 366 of the needle cover 312 are planar, although other suitable shapes and configurations may be utilized. The needle cover clip(s) 364 are configured to restrict the axial movement of the needle cover 312 relative to the cassette body 314. The cassette body 314 further includes motor body rib(s) 368 and upper housing shell rib(s) 370, which are configured to engage corresponding portions of the motor body 302 and the upper housing shell 320 to aid in the assembly of the device 300. The cassette body 314 also includes syringe holder stop(s) 372, which are configured to engage portions of the syringe holder 310 to limit the axial movement of the syringe holder 310 relative to the cassette body 314. Although not shown in FIG. 48, the locking clip 64 may also be utilized with the drug delivery device 300.

Referring to FIGS. 41-46, the cap 316 is similar to and functions similarly to the cap 18 described above and shown in FIGS. 1A-24. The cap 316 includes a protrusion(s) 374 that is received by a cap opening(s) 376 defined by the needle cover 312, which is positioned 90 degrees relative to the position of those elements of the cap 18 of FIGS. 1A-24. The protrusion(s) 374 of the cap 316 is configured to engage the needle cover 312 upon movement of the needle cover 312 from the pre-use position to the actuation position. For instance, with the device 300 in the storage position with the cap 316 secured to the lower housing shell 322, if the device is dropped or impacted to apply a force to the needle cover 312, the lever actuation member 308, and/or other component, the protrusion(s) 374 restricts movement of the needle cover 312, which prevents any unintended actuation of the device 300. The cap 316 further includes a retainer clip(s) 378 and a rib(s) 380 for engaging a wing(s) 382 of the retainer 318. The retainer clip(s) 378 and the rib(s) 380 secure the retainer 318 to the cap 316 and prevent any movement or wobbling of the retainer 318 relative to the cap 316. The retainer 318 is configured to remove the RNS 58 when the cap 316 is removed from the lower housing shell 322. The cap 316 includes a lower housing shell clip(s) 384 for engaging the lower housing shell 322 to secure the cap 316 to the lower housing shell 322. The upper housing shell 320 and the lower housing shell 322 are similar and function similarly to the upper housing shell 46 and the lower housing shell 28 discussed above and shown in FIGS. 1A-24. The lower housing shell 322, however, has a cap interface 386 to receive the lower housing shell clip(s) 384 of the cap 316.

Figure 47:
FIG. 47 is a cross-sectional view of the drug delivery device of FIG. 25, showing an injection position of the device.
Figure 48:
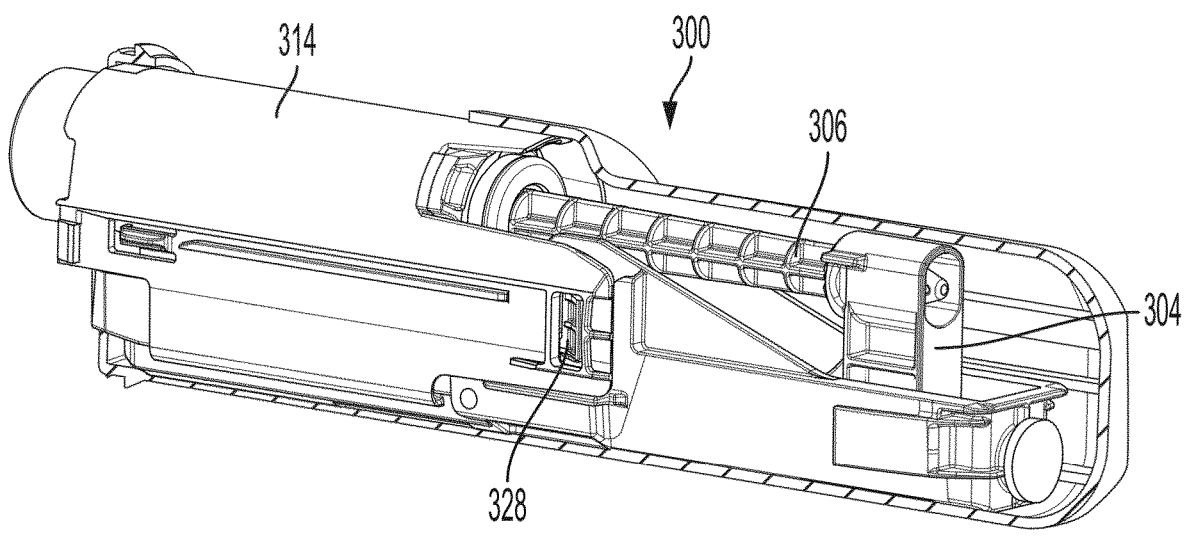
FIG. 48 is a partial cross-sectional view of the drug delivery system of FIG. 25.
Figure 49:
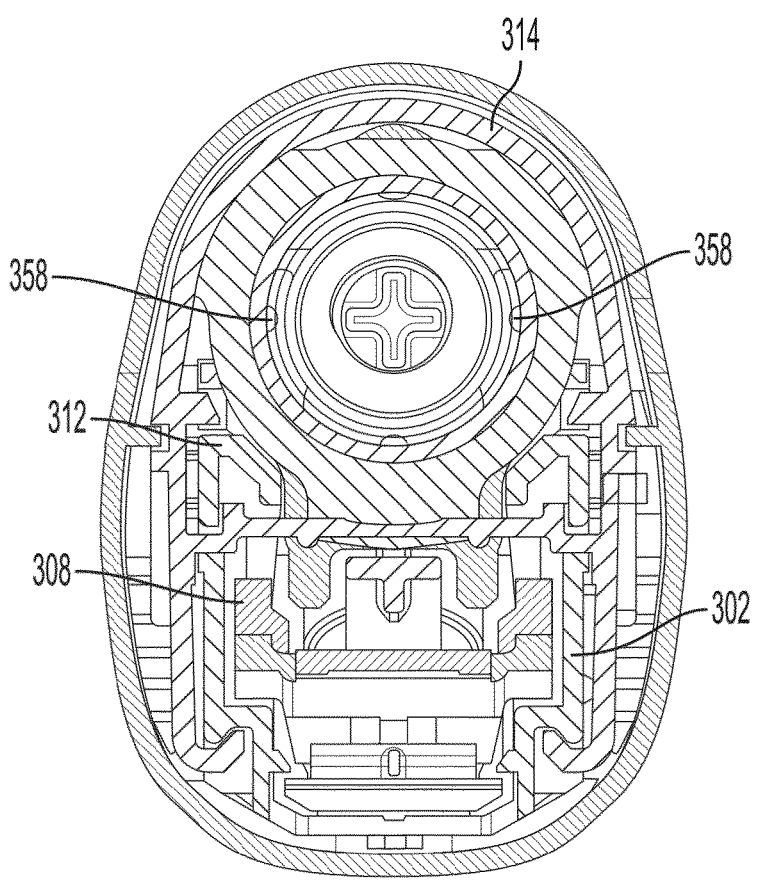
FIG. 49 is a cross-sectional view of the drug delivery system of FIG. 25.

Referring to FIG. 47, the drug delivery device 300 is shown in an injection position. The injection depth of the cannula 56 is determined by contact between the syringe holder 310 and the cassette body 314 at point X and contact between the needle cover 312 and the syringe holder 310 at point Y.

Referring to FIG. 47, the drug delivery device 300 includes an audio indicator member 388, which is similar to and functions similarly to the audio indicator member 94 described above and shown in FIGS. 1A-24. In the same manner as the audio indicator member 94, which is described above, the audio indicator member 388 of the drug delivery device 300 is configured to provide an audible indication to a user when the device 300 transition to the post-use position. The audio indicator member 388 is configured to engage rib(s) 390 of the cassette body 314 when the device 300 is in the injection position thereby deflecting the audio indicator member 388. The audio indicator member 388 disengages from the rib(s) 390 of the cassette body 314 and contacts the lower housing shell 322 to provide an audible click when the drug delivery device 300 transition from the injection position to the post-use position. However, a distal end 392 of the rib(s) 390 of the cassette body 314 is angled rearward toward the upper housing shell 320, which beneficially provides a louder audible click compared to the arranged of the rib(s) 96 of the cassette body 26 discussed above in connection with FIGS. 1A-24.

In one aspect or embodiment, an angle Z of the distal end 392 of the rib(s) 390 of the cassette body 314 relative to a plane extending perpendicularly to a longitudinal axis of the device 300 is greater than 5 degrees. In one aspect or embodiment, the angle Z of the distal end 392 of the rib(s) 390 is greater than 10 degrees. In one aspect or embodiment, the angle Z of the distal end 392 is 25 degrees.

Elements of one disclosed aspect can be combined with elements of one or more other disclosed aspects to form different combinations, all of which are considered to be within the scope of the present invention.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A drug delivery device comprising:
   a housing;
   a syringe assembly comprising a barrel, a stopper, a cannula, and a rigid needle shield receiving at least a portion of the cannula, at least a portion of the syringe assembly positioned within the housing;
   a drive assembly configured to move the stopper within the barrel upon actuation of the drive assembly, at least a portion of the drive assembly positioned within the housing;
   a cap secured to the housing, the cap comprises an outer portion defining an interior space and a retainer comprising a body having a proximal end and a distal end, the retainer having a removal projection arranged between the proximal end and the distal end, the removal projection configured to remove the rigid needle shield upon axial movement of the outer portion of the cap away from the housing, the body of the retainer comprises a first end and a second end positioned opposite the first end, the removal projection extending radially inward from the body of the retainer via a removal arm, the removal arm extending radially inward and in a direction extending from the second end of the body of the retainer towards the first end of the body of the retainer;
   a needle cover having a pre-use position where the cannula and the body of the retainer are positioned within the needle cover, an actuation position where the drive assembly is actuated, and a post-use position where the cannula is positioned within the needle cover, wherein the outer portion receives a portion of the needle cover, the outer portion configured to prevent movement of the needle cover from the pre-use position to the actuation position; and
   a syringe holder positioned within the housing, the syringe holder receiving the syringe assembly, the syringe holder moveable relative to the housing, wherein the syringe holder is disengaged with the drive assembly when the outer portion is secured to the housing, and wherein the syringe holder is engaged with the drive assembly immediately upon the axial movement of the outer portion away from the housing.

2. The drug delivery device of claim 1, wherein the outer portion includes a protrusion received by a cap opening defined by the needle cover, the protrusion of the outer portion is configured to engage the needle cover upon the movement of the needle cover from the pre-use position to the actuation position.

3. The drug delivery device of claim 1, wherein a portion of the retainer is received within the interior space of the outer portion of the cap, and wherein the retainer is secured to and axially moveable relative to the outer portion.

4. The drug delivery device of claim 3, wherein the outer portion comprises a retaining tab received by a retainer opening defined by the body of the retainer, the retaining tab is disengaged from the body of the retainer when the outer portion is secured to the housing, the retaining tab of the outer portion is configured to engage the retainer upon the axial movement of the outer portion away from the housing and upon axial movement of the outer portion relative to the retainer.

5. The drug delivery device of claim 1, wherein the retainer comprises a pair of wings extending radially outward from the body of the retainer, each wing of the pair of wings configured to engage a rib extending radially inward from a body of the outer portion.

6. The drug delivery device of claim 4, wherein the retaining tab extends radially outward through the retainer opening of the retainer upon the axial movement of the outer portion of the cap away from the housing and upon the axial movement of the outer portion relative to the retainer.

7. The drug delivery device of claim 4, wherein the retaining tab of the outer portion is secured to a body of the outer portion via an extension arm, the retaining tab moveable radially inward via the extension arm.

8. The drug delivery device of claim 1, wherein the retainer comprises a flange engaged with the outer portion when the outer portion is secured to the housing.

9. The drug delivery device of claim 8, wherein the flange of the retainer is spaced from the outer portion upon the axial movement of the outer portion away from the housing.

10. The drug delivery device of claim 1, wherein a surface of the removal projection is planar, and wherein a corresponding surface of the rigid needle shield is planar.

11. The drug delivery device of claim 1, wherein the removal projection is moveable relative to the body of the retainer via the removal arm.

12. The drug delivery device of claim 1, wherein a surface of the removal projection is configured to engage a corresponding surface of the rigid needle shield to remove the rigid needle shield upon the axial movement of the outer portion of the cap away from the housing, the surface of the removal projection is disengaged from the corresponding surface of the rigid needle shield when the outer portion is secured to the housing.

13. The drug delivery device of claim 12, wherein a protrusion is configured to be removed from a cap opening before the surface of the removal projection engages the corresponding surface of the rigid needle shield upon the axial movement of the outer portion away from the housing.

14. The drug delivery device of claim 1, wherein the outer portion comprises one of a lock protrusion and a lock recess and the housing comprises the other of the lock protrusion and the lock recess, the lock protrusion received by the lock recess to secure the outer portion to the housing, and wherein the lock protrusion is separated from the lock recess before a surface of the removal projection engages a corresponding surface of the rigid needle shield upon the axial movement of the outer portion away from the housing.

* * * * *